US006630120B1

(12) United States Patent
Bartus et al.

(10) Patent No.: US 6,630,120 B1
(45) Date of Patent: Oct. 7, 2003

(54) AGENTS TO INCREASE THE UPTAKE OF PHARMACEUTICALS AND DIAGNOSTIC SUBSTANCES INTO SOLID TUMORS

(75) Inventors: Raymond T. Bartus, Sudbury, MA (US); Dwaine F. Emerich, Cranston, RI (US)

(73) Assignee: Alkermes, Inc., Cambridge, MA (US)

( * ) Notice: Subject to any disclaimer, the term of this patent is extended or adjusted under 35 U.S.C. 154(b) by 0 days.

(21) Appl. No.: 09/264,102

(22) Filed: Mar. 8, 1999

(51) Int. Cl.$^7$ .................. A61K 38/08; A61K 49/00; A61K 51/00
(52) U.S. Cl. ................ 424/1.11; 424/9.1; 514/15
(58) Field of Search ................ 424/1.41, 1.69, 424/9.34, 9.341, 9.411, 649, 1.11, 1.73, 9.1; 514/15; 530/314; 930/DIG. 600, DIG. 601, DIG. 602

(56) References Cited

U.S. PATENT DOCUMENTS

| | | | |
|---|---|---|---|
| 3,364,193 A | 1/1968 | Hempel et al. | 530/314 |
| 4,923,963 A | 5/1990 | Stewart et al. | 530/314 |
| 5,112,596 A | 5/1992 | Malfroy-Camine | 424/2 |
| 5,162,497 A | 11/1992 | Coy et al. | 530/314 |
| 5,268,164 A | 12/1993 | Kozarich et al. | 424/9 |
| 5,506,206 A | 4/1996 | Kozarich et al. | 514/15 |
| 5,585,355 A | 12/1996 | Graney | 514/15 |
| 5,686,416 A | 11/1997 | Kozarich et al. | 514/15 |

FOREIGN PATENT DOCUMENTS

| | | | |
|---|---|---|---|
| WO | WO 89/09231 | | 10/1989 |
| WO | 90/03801 A1 | * | 4/1990 |
| WO | WO 91/16355 | | 10/1991 |
| WO | 98/55112 A1 | * | 12/1998 |

OTHER PUBLICATIONS

Khawli et al. Effect of Seven New Vasoactive Immunoconjugates . . . Cancer Supplement. vol. 73, No. 3, pp. 824–831, Feb. 1, 1994.*

Kinuya et al. Persistent Distension and Enhanced Diffusive Extravasation . . . Oncology Research. 1998, vol. 10, pp. 551–559.*

Araki, T., et al. "Newly Developed Transarterial Chemoembolization Material:CDDP–Lipiodol Suspension," *Gastrointestinal Radiol.* 4:46–48, 1989.

Mavligit, G.M., "Durable Hepatic Tumor Regression After Arterial Chemoembolization–Infusion in Patients with Islet Cell Carcinoma of the Pancreas Metastatic to the Liver." *Cancer* 72(2):375–380, 1993.

Yalowich, J.C., "Teniposide (VM–26)– and Etoposide (VP–16–213)–Induced Augmentation of Methotrexate Transport and Polyglutamylation in Ehrlich Ascites Tumor Cells in vitro." *Cancer Research* 42:3648–3653, 1982.

Jain, R.K., "Delivery of Molecular Medicine to Solid Tumors," *Science* 271:1079–1080 (1996).

Jain, R.K., "1995 Whitaker Lecture: Delivery of Molecules, Particles, and Cells to Solid Tumors," *Annals of Biomedical Engineering* 24:457–473 (1996).

Nomura, T., et al., "Effect of Particle Size and Charge on the Disposition of Lipid Carriers After Intratumoral Injection into Tissue–isolated Tumors," *Pharmaceutical Research* 15(1) :128–132 (1998).

Brown, J.M. and Giaccia, A.J., "The Unique Physiology of Solid Tumors: Opportunities (and Problems) for Cancer Therapy," *Cancer Research* 58:1408–1416 (1998).

Jain, R.K., "Barriers to Drug Delivery in Solid Tumors," *Scientific American* 271(1) :58–65 (1994).

(List continued on next page.)

*Primary Examiner*—Jeffrey E. Russel
(74) *Attorney, Agent, or Firm*—Hamilton, Brook, Smith & Reynolds, P.C.

(57) ABSTRACT

Agents, such as bradykinin agonists, increase the transport of pharmaceutical or diagnostic substances that are initially in the bloodstream of a host animal into the interstitial spaces of non-central nervous system solid tumors that may reside in these hosts. A particularly efficacious agent is Cereport™.

20 Claims, 15 Drawing Sheets-

OTHER PUBLICATIONS

Kyle, et al., "Design and Conformational Analysis of Several Highly Potent Bradykinin Receptor Antagonists," *J. Med. Chem.* 34(3) :1230–1233 (1991).

Wahl, M., et al., "Effects of Bradykinin on Pial Arteries and Arterioles In Vitro and In Situ," *J. Cere. Blood Flow and Metab.* 3:231–237 (1983).

Unterberg, A. and Baethmann, A.J., "The Kallikrein–Kinin System as Mediator in Vasogenic Brain Edema," *J. Neurosurg.* 61:87–96 (1984).

Unterberg, A., et al., "Effects of Bradykinin on Permeability and Diameter of Pial Vessels In Vivo," *J. Cere. Blood Flow and Metab.* 4:574–585 (1984).

Wahl, M., et al., "Cerebrovascular Effects of Bradykinin," *Neural Regulation of Brain Circulation*, C. Owman and J.E. Hardebo, eds. Elsevier Science Publ., pp. 419–430 (1986).

Olesen, S.P. and Crone, C., "Substances that Rapidly Augment Ionic Conductance of Endothelium in Cerebral Venules," *Acta Physiol Scand.* 233–241 (1986).

Wahl, M., et al., "Effects of Bradykinin on Cerebral Haemodynamics and Blood–Brain Barrier Function," In: Peptidergic Mechanisms in Cerebral Circulation (Edwinssen and McCulloch, eds.) Chichester, Herwood, pp. 166–190 (1987).

Wahl, M., et al., "Mediators of Blood–Brain Barrier Dysfunction and Formation of Vasogenic Brain Edema," *J. Cere. Blood Flow and Metab.* 8:621–634 (1988).

Raymond, J.J., et al., "Pharmacological Modification of Bradykinin Induced Breakdown of the Blood–Brain Barrier," *Can. J. Neuro. Sci.* 13:214–220 (1986).

Saria, A., et al., "Vascular Protein Leakage in Various Tissues Induced by Substance P, Capsaicin, Bradykinin, Serotonin, Histamine and by Antigen Challenge," *Naunyn–Schniedeberg's Arch. Pharmacol.*, 324:212–218 (1983).

Schurer, L., et al., "Blood–Brain Barrier Permeability and Vascular Reactivity to Bradykinin after Pretreatment with Dexamethasone," *Acta Neuropathol.* 77:576–581 (1989).

Marceau, et al., "Pharmacology of Kinins: Their Relevance to Tissue Injury and Inflammation," *Gen. Pharmac.*, 14(2) : 209–229 (1983).

Hiesiger, et al., "Opening the Blood–Brain and Blood–Tumor Barriers in Experimental Rat Brain Tumors: The Effect of Intracarotid Hypersmolar Mannitol on Capillary Permeability and Blood Flow," *Annals Neurology* 19(1) :50–59 (1986).

Unterberg, A., et al., "Blood Flow, Metabolism, and Function of the Brain During Cerebral Administration of Bradykinin," *Advances in Neurosurgery* 13:326–329 (1985).

Chemical Abstracts, vol. 105, No. 19, Nov. 10, 1986, Columbus, OH, U.S., Abstract No. 164987q.

Rhaleb, et al., "Structure–Activity Studies on Bradykinin and Related Peptides: Agonist," *Br. J. Pharmacol.* 99:445–448 (1990).

Drapeau, et al., "[Phe$^8$ $\Psi$ (CH$_2$–NH)Arg$^9$] Bradykinin . . . ," *European J. Pharmacology* 155:193–195 (1988).

Elliott, P.J., et al., "Dissociation of Blood–Brain Barrier Permeability and the Hypotensive Effects of the Bradykinin B2 Agonist, RMP–7," *Immunopharmacology* 33:205–208 (1996).

Doctrow, S.R., et al., "The Bradykinin Analog RMP–7 Increases Intracellular Free Calcium Levels in Rat Brain Microvascular Endothelial Cells," *J. Pharmacology and Experimental Techniques* 271:229–237 (1994).

* cited by examiner

FIGURE 1
Significant Carboplatin Uptake
Following 10 minute Infusion of Cereport
(Carbo given at T=2 min)
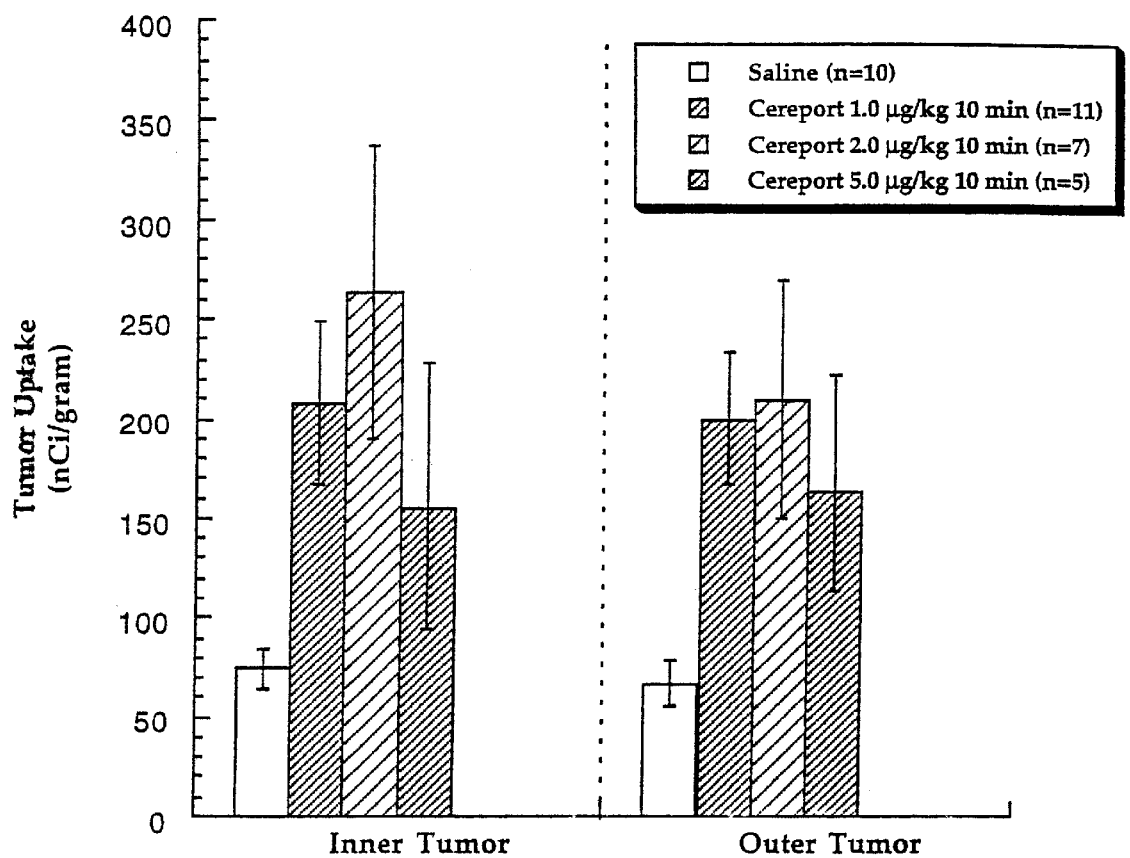
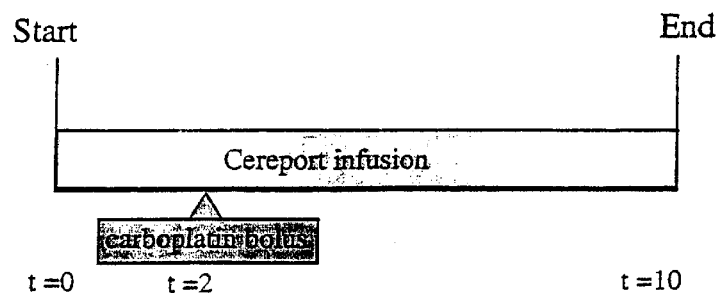

FIGURE 4
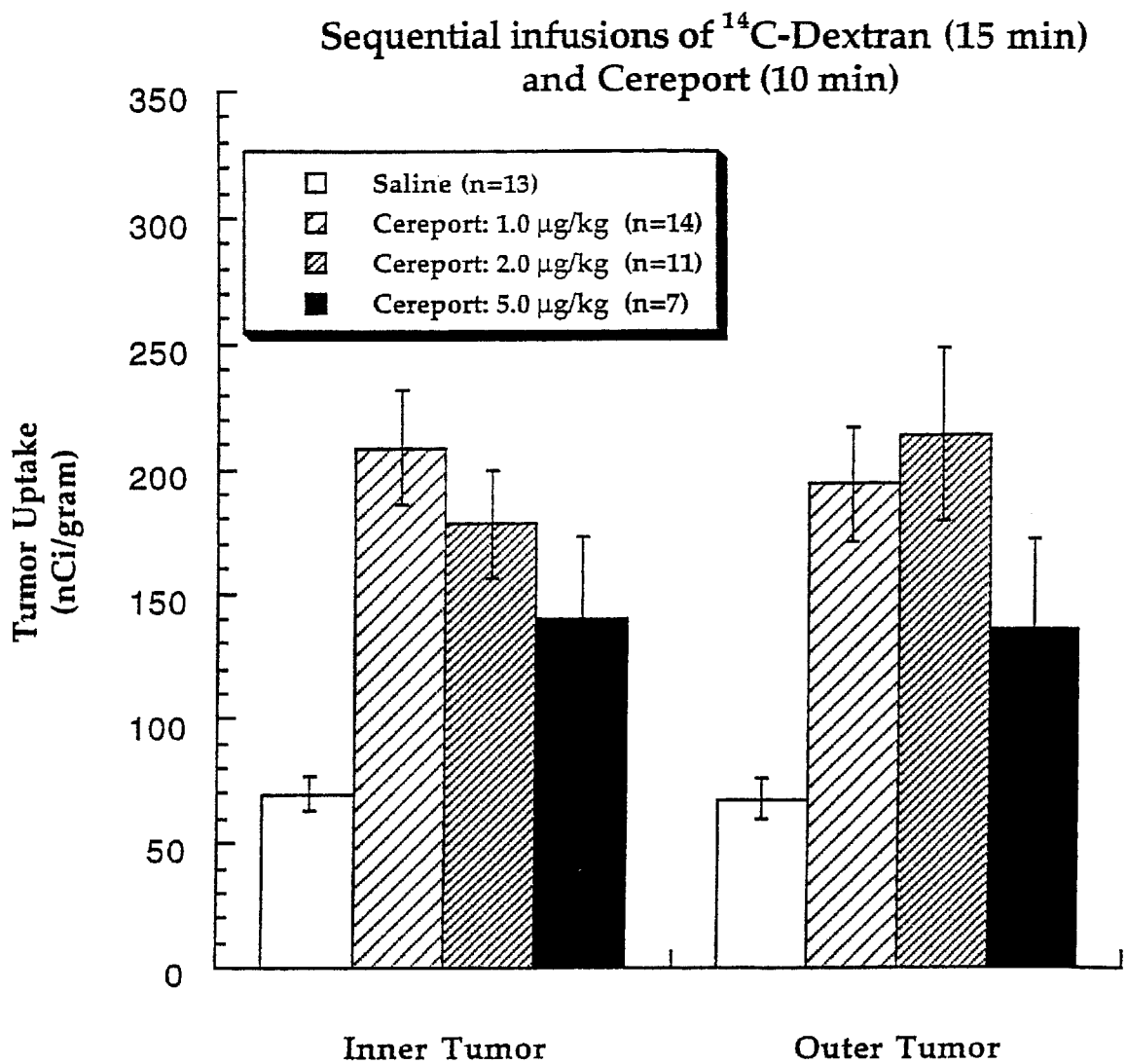
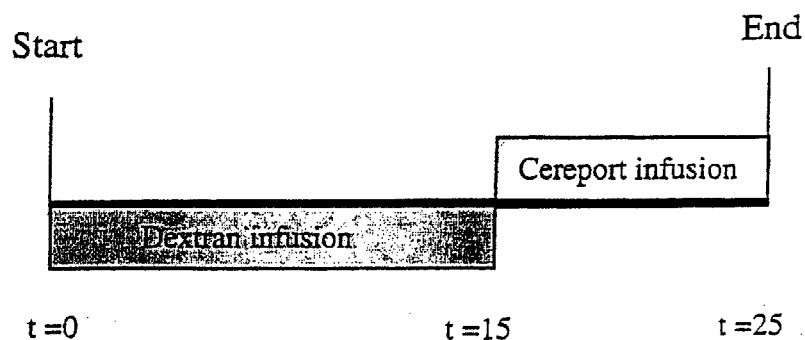

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthesized
<223> OTHER INFORMATION: Position 3 is Hydroxyproline
<223> OTHER INFORMATION: Position 5 is Thienylalanine
<223> OTHER INFORMATION: Position 8 substituent is a 4-methyl group
<223> OTHER INFORMATION: Position 8-9 Reduced peptide bond
<221> NAME/KEY: VARIANT
<222> LOCATION: (1)...(9)
<223> OTHER INFORMATION: Xaa = Any Amino Acid

<400> SEQUENCE: 1

Arg Pro Xaa Gly Xaa Ser Pro Tyr Arg
 1               5

<210> SEQ ID NO 2
<211> LENGTH: 9
<212> TYPE: PRT
<213> ORGANISM: Human
<300> PUBLICATION INFORMATION:
<301> AUTHORS: Marceau, et al.
<302> TITLE: Pharmacology of Kinins: Their Relevance to Tissue
<303> JOURNAL: General Pharmacology
<304> VOLUME: 14
<305> ISSUE: 2
<306> PAGES: 209-229

<400> SEQUENCE: 2

Arg Pro Pro Gly Phe Ser Pro Phe Arg
 1               5

AGENTS TO INCREASE THE UPTAKE OF PHARMACEUTICALS AND DIAGNOSTIC SUBSTANCES INTO SOLID TUMORS

BACKGROUND OF THE INVENTION

Cancer is still one of the most difficult diseases to understand, diagnose and treat. After decades of intense research interest, the causes and prevention of this disease or these diseases remain elusive, despite several notable advances in our knowledge of the physiological processes that underlie the disease.

One of the reasons for the lack of understanding of cancer or its adequate treatment is that it is manifested in various physical states. Cancer can occur as diffuse cells, e.g. the leukemias, or as solid tumors. The solid tumors can reside at various anatomic locations or sites within the body. These tumors can exist within or be contiguous to an organ that is normally found within the body.

The solid tumors quickly acquire their own blood supply and vasculature (arterioles, capillaries and venules) when they have achieved a minimum size (otherwise they use the body's normal blood supply and vasculature). This tumor blood vasculature has some properties that resemble those for the vasculature of normal organs of the body. However, the vasculature of solid tumors also has properties that are dissimilar from that of normal organs. The distribution of blood vessels is not uniform in solid tumors. The vasculature of solid tumors can have tortuous pathways, blind terminations and abnormal shunts between the arterial and the venous portions of the vasculature. Blood flow is markedly slowed in the blood vessels in solid tumors. The viscosity of the blood in the vasculature of solid tumors also appears to be higher than that for blood in normal tissues. In addition, vessel walls within solid tumors can be leaky to molecules contained within the bloodstream or they can be quite impervious to such molecules. Often, the leakiness and imperviousness occur within the same blood vessel within the same solid tumor.

Another unique feature of solid tumors is the high interstitial pressure that exists in comparison to the interstitial pressure in normal organs. The pressure for fluid flow that exists within the spaces that surround the cells that comprise the solid tumor is much higher in the internal spaces of the tumor than within the internal spaces of normal tissues and organs. The high interstitial pressure in the internal spaces of solid tumors greatly retards the movement of molecules that are present in the bloodstream into the internal spaces of solid tumors. This retardation particularly affects those molecules that are transported from the bloodstream into the internal spaces of solid tumors primarily by the movement of the molecules down a pressure gradient from the bloodstream to the interstitial spaces of the solid tumor. Because of the high interstitial pressure in solid tumors, such movement becomes much slower or nonexistent.

For the above reasons, the delivery of therapeutic or diagnostic molecules from the bloodstream to the internal spaces of solid tumors, particularly non-central nervous system solid tumors, does not readily occur. At the present time, it is difficult to deliver therapeutic or diagnostic pharmaceuticals to the tumor cells that constitute solid tumors. It is likewise difficult to maintain sufficient amounts of such pharmaceuticals in the vicinity of the tumor cells long enough for the tumor cells to be affected by the pharmaceuticals. Primarily, this is because tumor cells of the solid tumors reside in the extravascular region, often at some distance from a given blood vessel in these tumors.

It is readily apparent that improved delivery of molecules, particularly therapeutic or diagnostic pharmaceutical molecules, from the bloodstream to the internal spaces of solid tumors, would be an advancement in the diagnosis and treatment of these solid tumors. This is particularly true for the delivery of molecules to the internal spaces of non-central nervous system solid tumors. The administration of such molecules into the bloodstream of the host followed by their transport to the internal spaces of solid tumors would be a significant gain in solid tumor treatment and diagnosis. This delivery procedure would be much less invasive than the physical administration of these molecules directly into the solid tumor mass with subsequent loss from the tumor to the bloodstream.

SUMMARY OF THE INVENTION

The present invention pertains to a method of increasing the transport of a molecule from the bloodstream of a host to the internal spaces of a non-central nervous system solid tumor that is present in the host. This method comprises intravascular co-administration to the host of an effective amount of an agent that increases such transport of the molecule. The molecule to be delivered to the tumor can be an endogenous molecule or an exogenous molecule that is co-administered sequentially or simultaneously with the agent.

An advantage of the present invention is that it provides a practical means of increasing the transport of a molecule from the bloodstream to the internal spaces of a non-central nervous system solid tumor by the intravascular administration of the agent while co-administering a molecule of therapeutic, prophylactic or diagnostic value.

Preferred agents are bradykinin agonists. Particularly preferred bradykinin agonists are compositions which are peptides having a core sequence of amino acids or amino acid analogs. In the core peptide, the sequence is arginine-proline-hydroxyproline-glycine-thienylalanine-serine-proline-4-Me-tyrosine$\psi$($CH_2NH$)arginine (Seq. ID No: 1), from N-terminal to C-terminal, where $CH_2NH$ denotes a reduced peptide bond between the 4-Me-tyrosine and arginine amino acids. This peptide, which is an analog of bradykinin, is referred to herein, for convenience, as Cereport™. Conformational analogs of this, sequence are also preferred bradykinin agonists, provided they have the property of increasing the transport of a molecule from the bloodstream of a host to the internal spaces of a non-central nervous system solid tumor.

BRIEF DESCRIPTION OF THE DRAWINGS

FIG. 1 is a diagrammatic representation of the amount of carboplatin uptake into the inner and outer portions of an implanted tumor for various amounts of administered Cereport™. The time course of carboplatin administration and Cereport™ infusion is also diagrammatically represented.

FIG. 4 is a diagrammatic representation of the amount of dextran uptake into the inner and outer portions of an implanted tumor for various amounts of administered Cereport™. The sequential time course of dextran administration and Cereport™ infusion is also diagrammatically represented.

DETAILED DESCRIPTION OF THE INVENTION

Figure 2:
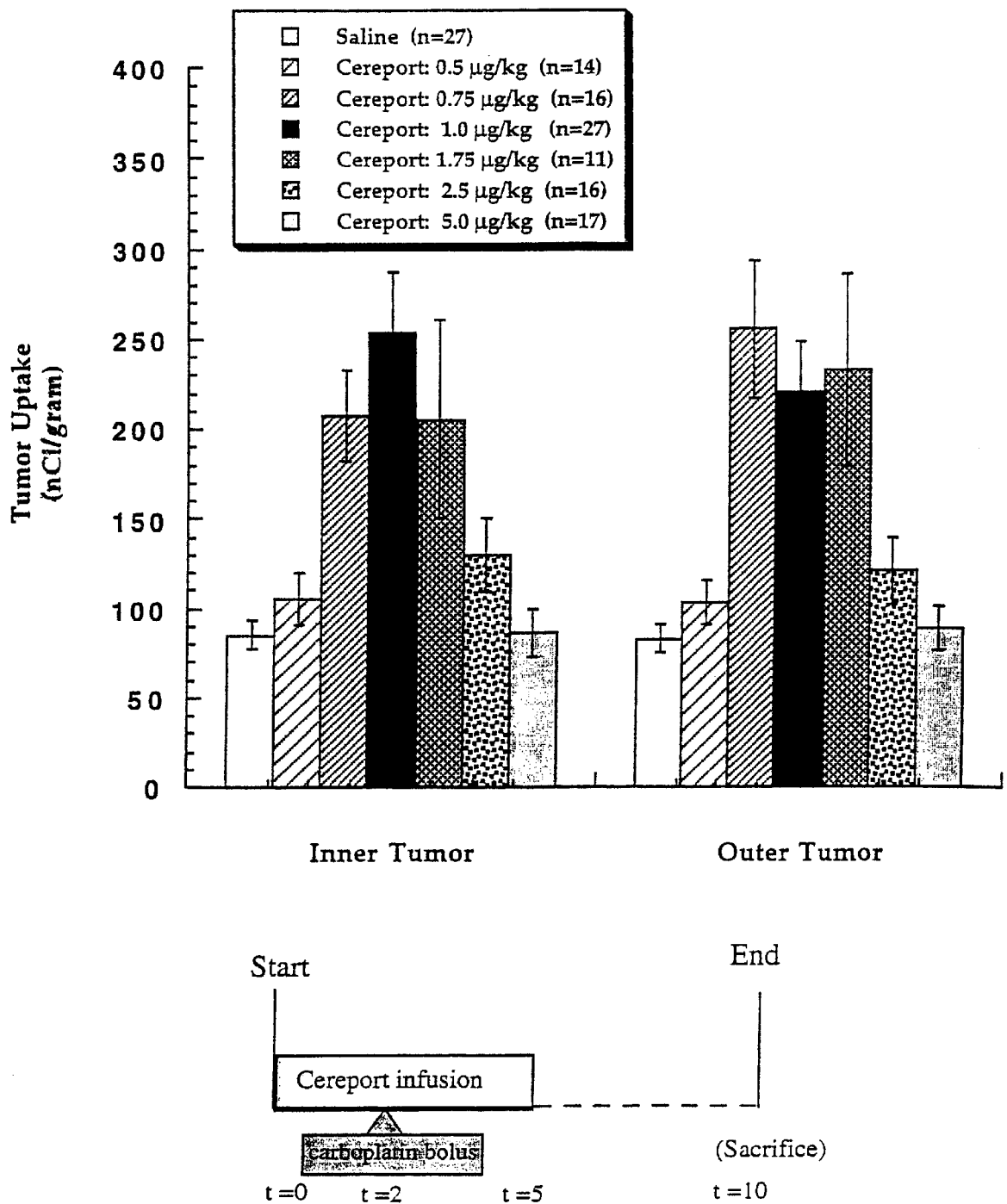
FIG. 2 is another diagrammatic representation of the amount of carboplatin uptake into the inner and outer portions of an implanted tumor for various amounts of administered Cereport™. The time course of carboplatin administration and Cereport™ infusion is also diagrammatically represented.

This invention relates to a method for increasing the transport of a molecule from the bloodstream of a host to the internal spaces of a non-central nervous system solid tumor that is present in the host. The internal spaces of a non-central nervous system solid tumor include the interstitial spaces between cells and the tumor cells, themselves. The host can be any animal. Examples of hosts include mammals, such as humans and domestic animals (e.g. dog, cat, cow or horse), as well as animals intended for experimental purposes (e.g. mice, rats, rabbits).

The molecule in the host's bloodstream can be exogenous to the host. For example, it can be a pharmaceutical substance which has a therapeutic or prophylactic effect on a tumor. These tumors are solid tumors with their own intimate blood supply. Such tumors have blood vessels which supply nutrients and other materials needed by the tumor for maintenance and growth. The molecule in the host's bloodstream is more readily transported from these blood vessels to the internal spaces of the tumor by the co-administration of an effective amount of an agent of this invention, thereby allowing entry of the pharmaceutical or diagnostic substance into the tumor. Pharmaceutical substances, particularly chemotherapeutic substances, delivered to the internal spaces of the tumor cause various physiological processes which lead to the arrest, stabilization, shrinkage, if not eradication, of the tumor. Other pharmaceutical substances include hydrophilic substances that retard tumor growth when they are delivered to the internal spaces of the tumor. In essence, the agents that facilitate transport, in this invention, lower the blood vessel barrier of the tumor to the penetrability of pharmaceutical and diagnostic substances into the interstitial spaces of the tumor and thence to the tumor cells. By lowering this penetrability barrier, pharmaceutical and diagnostic substances more readily reach the tumor interstitial spaces and tumor cells in higher relative concentrations than without the administration of the agents that facilitate transport of the substances. Once in the interstitial space, the substances can interact with specific receptor molecules on the tumor cells to produce a pharmaceutical effect or serve as a passive location marker.

Classes of pharmaceutical substances which can be used in this invention include chemotherapeutic substances, cytokines, taxoteres, oligonucleotides, antibody fragments, proteins, peptides, radioactive compounds, and other classes of agents used to treat or prevent a solid tumor. Examples of chemotherapeutic substances include adriamycin, methotrexate, cyclophosphamide, etoposide, carboplatin and cisplatin.

The molecules in the host's bloodstream can be diagnostic imaging or contrast substances. Examples of diagnostic substances include substances that are labelled with radioactivity, such as 99-Tc glucoheptonate, substances used in positron emission tomography (PET) such as 68-Ga, or substances used in Magnetic Resonance Imaging (MRI) procedures such as gadolinium doped chelation agents (e.g., Gd-DTPA). Iodinated compounds used in computed tomography (CT) procedures can also be used.

The route of administration of exogenous molecules to the host's bloodstream can be parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) will depend, at least in part, on the route by which it is administered.

The agents of this invention, including Cereport™ or conformational analogs thereof, can also be administered by one of the traditional routes of administration. That is, the agents of this invention can be administered by such techniques as intravascular, subcutaneous or intramuscular injections, oral, transdermal or intranasal administrations, and inhalation or sustained release routes. These routes of administration provide a variety of available options for delivering the agents of this invention into the bloodstream of the host.

The administration of the exogenous molecule and the administration of an agent of this invention to the host's bloodstream can occur simultaneously or sequentially in time. For example, a therapeutic drug can be administered orally in tablet form while an intravenous administration of an agent of this invention is given some time later. This is to allow time for the drug to be absorbed from the gastrointestinal tract and taken up by the bloodstream before the agent is given that increases the transport of the drug through the bloodstream to the internal spaces of a non-central nervous system solid tumor. Alternatively, the agent of this invention can be administered before or at the same time as an intravascular injection of a drug when such an administration sequence maximizes the uptake of the drug into the internal spaces of the non-central nervous system solid tumor. Thus, the term "co-administration" is used herein to mean that the agent of this invention and the exogenous molecule will be administered at times that will achieve significant concentrations in the blood of both the agent and the exogenous molecule for producing the simultaneous effects of increasing the transport of the molecule from the bloodstream to the internal spaces of the tumor and allowing the maximum passage of the exogenous molecule from, the blood to the cells of the tumor. Preferably, the pharmaceutical or diagnostic agent is administered to the host during or just prior to the administration of the agents of this invention. These particular administration patterns usually maximize the efficacy of the agents in allowing the pharmaceutical or diagnostic agent to enter the interstitial spaces of the tumor.

Compounds are termed agonists when they increase or elicit a physiological activity similar to that elicited by an endogenous ligand. In the present invention, the agonistic process is believed to operate through an initial cell surface receptor mediated event. An endogenous ligand and agonists, in this invention, are bradykinin and bradykinin analogs. Bradykinin is a naturally occurring peptide comprised of nine amino acids with the following sequence: Arginine-Proline-Proline-Glycine-Phenylalanine-Serine-Proline-Phenylalanine-Arginine (SEQ ID NO: 2)(Lehninger, A. L., *Biochemistry*, p. 97, (1975)). An analog is a structural derivative of a parent compound. Analogs of bradykinin can be compounds which are derivatives of the number and/or sequence of amino acids in the bradykinin structure mentioned above which have a similar or enhanced effect on the transport of molecules from the bloodstream to the internal spaces of non-central nervous system solid tumors. Modification of the bradykinin molecule can be done by changing or modifying amino acids, modifying peptide bonds, adding C terminal and/or N-terminal extensions, etc.

Specific compositions that are useful in this invention are referred to as Cereport™ or conformational analogs thereof. These compositions, in particular, increase the transport of molecules of interest from the bloodstream to the internal spaces of non-central nervous system solid tumors. The increased transport of molecules from the bloodstream to the internal spaces of the tumor that occurs as a result of the administration of these compositions is believed to be mediated by receptor molecules, possibly the $B_2$ receptors, located on the surface of endothelial cells that form the vasculature of non-centralnervous system solid tumors. The interaction between these receptors and the compositions of this invention apparently alters transport properties of the endothelial cells and/or epithelial cells thereby increasing the movement from the bloodstream into the interstitial spaces of the tumor for molecules such as the molecule of interest. These molecules more freely enter and remain in these interstitial spaces as a result of this interaction at the receptors or as a result of some yet undetermined event that occurs following the molecular bonding or recognition that occurs between the cellular receptor or recognition molecule and the agents of this invention.

The substance known as bradykinin can increase the transport of molecules of interest from the bloodstream to the internal spaces of non-central nervous system solid tumors. This treatment increase probably occurs by the same mechanism as that for Cereport™ or conformational analogs thereof. That is, bradykinin probably interacts at the same receptors ($B_2$) as Cereport™ or its conformational analogs to cause an alteration of the transport process so that certain molecules can more easily leave the bloodstream to enter the interstitial fluid of the tumor. For this reason, Cereport™, or its conformational analogs and bradykinin may be considered to be pharmacological agonists.

Cereport™ and certain conformational analogs, like bradykinin, are peptides having a sequence of amino acids. This sequence of amino acids has such a conformation that it can interact with molecules associated with the transport process e.g. a receptor molecule, to effect an increase in the transport into a tumor's internal spaces of a molecule of interest that resides in or is administered such that the molecule reaches the bloodstream. The specific sequence of amino acids of the various Cereport™ or conformational analogs confers the proper conformation to them so they interact with the molecules associated with the transport process to cause an increase in the transport of a molecule of interest from the bloodstream to the internal spaces of non-central nervous system solid tumors. If the primary sequence is improper, the peptide will not adopt the proper conformation, thereby not effecting an increase in the subject transport process.

The proper conformation that allows Cereport™ or conformational analogs to interact with, for example, receptor molecules to effect an increase in the transport of a molecule of interest from the bloodstream to the internal spaces of a solid tumor puts a restriction on the structure of the amino acids that compose Cereport™ or conformational analog sequences of this invention. Only particular sequences of amino acids will fulfill the criterion for being a member of Cereport™ or conformational analogs; namely, that they allow the proper conformation so they can effect an increase in the transport of a molecule of interest from the bloodstream to the internal spaces of a non-central nervous system solid tumor.

Peptidomimetics of Cereport™ or conformational analogs, as well as bradykinin, can also be used as agents that increase the transport of a molecule from the bloodstream to the internal spaces of a non-central nervous system solid tumor. These peptidomimetics will have a conformation that allows them to interact with a receptor or recognition molecule in the manner of Cereport™, its conformational analogs or bradykinin.

A specific and preferred embodiment for use in this invention is the peptide with the linear amino acid sequence from N-terminal to C-terminal of: arginine-proline-hydroxyproline-glycine-thienylalanine-serine-proline-4-Me-tyrosineiψ(CH$_2$NH)-arginine (SEQ. ID NO: 1). This peptide is referred to herein as Cereport™. A method for synthesis of Cereport™ is given in U.S. Pat. No. 5,268,164, the synthetic route of which is incorporated herein by reference. However, other known preparative methods can be employed to produce Cereport™ or conformational analogs.

This peptide, Cereport™, differs from a conventional linear sequence of amino acids in the following ways: the fifth amino acid is thienylalanine which is similar to phenylalanine but where a thienyl group has replaced the phenyl group; the eighth amino acid is tyrosine which has been substituted with a methyl group at the 4 position; and the peptide bond between the eighth and ninth amino acids has been replaced with a reduced peptide bond isostere, i.e. $CH_2NH$. Peptide and peptidomimetic analogs of this embodiment are also part of this invention provided they allow the proper conformation in aqueous solution so they effect an increase in the transport of molecules of interest from the bloodstream to the internal spaces of non-central nervous system solid tumors. These latter compositions are termed "conformational analogs" of this embodiment.

The preferred transport agent Cereport™ differs from bradykinin in the following respects: at the third amino acid, hydroxyproline replaces proline; at the fifth amino acid, thienylalanine replaces phenylalanine; at the eighth amino acid, 4-Me-tyrosine replaces phenylalanine; and between the eighth and ninth amino acids, a reduced peptide bond replaces a conventional peptide bond. These differences make Cereport™ more effective for increasing the transport of a molecule from the bloodstream to the internal spaces of a solid tumor when compared to the transport properties of bradykinin. Much less of the Cereport™ is required to increase the transport of a molecule from the bloodstream to the internal spaces of a solid tumor and more of the molecule of interest is transported into the internal spaces of a solid tumor at a given administered amount of Cereport™ when compared to the same administered amount of bradykinin.

Characteristic features of Cereport™ or conformational analogs of this invention are important for Cereport™ or conformational analogs to allow the proper conformation to effect an increase in transport of a molecule of interest from the bloodstream to the internal spaces of a non-central nervous system solid tumor. The following modifications can be made to Cereport™, yet retain the proper conformation: the N-terminal arginine is replaced by an amino acid analog containing a guanidino side chain;) the second amino acid (proline) is replaced by hydroxyproline, dehydroproline, N-methylalanine or another proline analog; the third amino acid (hydroxyproline) is replaced by proline, dehydroproline, another proline analog, alanine, sarcasine or N-methylalanine; the fifth amino acid (thienylalanine) is replaced by another aromatic amino acid or a hydrophobic aliphatic amino acid; the sixth amino acid (serine) is replaced by glycine, threonine, alanine, allothreonine, asparagine, glutamine or analogs thereof; the seventh amino acid (proline) is replaced by hydroxyproline, dehydroproline, N-methylalanine or another proline analogue; the eighth amino acid (4-Me-tyrosine) is replaced by another O-alkyl tyrosine or a hydrophobic aliphatic amino acid; and the C-terminal arginine is replaced by an amino acid analog containing a guanidino side chain; and the peptidomimetic isosteric bond between the eighth amino acid (4-Me-tyrosine) and the C-terminal arginine ($\psi(CH_2NH)$) is replaced by $\psi(CSNH)$, $\psi(NHCO)$ or $\psi(CH_2S)$.

Within this general scheme for obtaining conformational analogs of Cereport™, it is preferred that the changes be limited to: β-cycloarginine, homoarginine, γ-hydroxyarginine, canavanine, $N^\omega$-amidinocitrulline, 2-amino-4-guanidobutanoic acid, citrulline or homocitrulline for the N-terminal or C-terminal arginine; hydroxyproline or dehydroproline for the second or seventh amino acids (proline); proline or dehydroproline for the third amino acid (hydroxyproline); dehydrophenylalanine, phenylalanine or another aromatic analog for the fifth amino acid (thienylalanine); glycine or threonine for the sixth amino acid (serine); and O-alkyl tyrosine for the eighth amino acid (4-Me-tyrosine).

With these specified amino acid designations, the proper conformation of Cereport™ or its conformational analogs is achieved so that Cereport™ or its conformational analogs can effect an increase in the transport of a molecule of interest from the bloodstream to the internal spaces of a non-central nervous system solid tumor. These amino acid positions and designations appear to be important for Cereport™ or its conformational analogs to allow the proper conformation so that the desired interaction with the receptor or recognition molecule can occur.

Another variation that is within this invention is the optional addition of one or more amino acids or analogs to the N-terminal arginine or the masking of the primary amino group of this arginine (e.g. acetylation). These additional amino acids are linked by typical peptide bonds to each other and to the N-terminal arginine, thus making the additional amino acids the N-terminal region of Cereport™ or conformational analog polypeptide. These additional amino acids are arginine or lysine or, if there are two additional amino acids, the N-terminal amino acid can be methionine. If a single amino acid is added and is arginine, it can be substituted with an acetyl or other masking agents (e.g. propyl, benzene, etc.) again or be the L-isomeric form. Preferred additional N-terminal amino acid groups are arginine-, acetyl arginine-, lysine-, arginine-arginine-, lysine-lysine, methionine-arginine- or methionine-lysine-, where these additional amino acids are of either D or L configuration.

The amino acids that constitute the core sequence of Cereport™ or conformational analogs of this invention should be formed as the L-isomer. The D-isomer can be substituted at some positions of the core sequence (e.g., position 8) and the resulting peptide will still retain its molecule transport activity.

This invention also pertains to pharmaceutical compositions suitable for administration to host animals to increase the transport of a molecule of interest from the bloodstream to the internal spaces of a non-central nervous system solid tumor. These pharmaceutical compositions contain one or more of Cereport™ or conformational analogs in a pharmaceutically acceptable carrier known to one of skill in the art. The pharmaceutical composition will often be given by injection into a blood vessel of the host animal. In particular, the pharmaceutical composition can be intravenously injected since Cereport™ or conformational analogs is not significantly degraded by angiotensin converting enzyme (ACE) known to be present in high concentrations in the lung. By contrast, bradykinin is significantly degraded by ACE and other enzymes, e.g. aminopeptidases or carboxypeptidases.

The quantity of Cereport™ or conformational analogs to be administered, and therefore packaged as units of the pharmaceutical composition, depends upon the efficacy of the chosen Cereport™ or conformational analogs, the type of tumor, the size and other individual variations of the host compared to the population of hosts as a whole and the molecule of interest to be transported into the interstitial spaces of the solid tumor. The actual amounts and concentrations of Cereport™ or conformational analogs in the pharmaceutical compositions can be readily ascertained by a person of skill in the art.

The pharmaceutical compositions of this invention can also contain the molecule of interest to be transported into the internal spaces of the solid tumor. In these compositions, both the molecule of interest and Cereport™ or conformational analog that fosters its entrance into the internal spaces of the solid tumor are included in a convenient package. This allows:the two substances to be co-administered so the efficiency of administration of these substances is maximized.

The amount of bradykinin agonist, Cereport™ or conformational analog administered to a host that is efficacious for increasing the transport of a molecule from the bloodstream to the internal spaces of a non-central nervous system solid tumor is well below the toxic level for that host. Thus, nontoxic dosages of bradykinin agonist, Cereport™ or conformational analogs can be administered without sacrificing transport activity.

An effective amount of an agent of this invention is that amount which will significantly increase the transport of the molecule of interest from the bloodstream to the internal spaces of the non-central nervous system solid tumor, i.e., to the interstitial spaces of the solid tumor tissue. There, the molecule of interest exerts a therapeutic or prophylactic effect or allows diagnostic procedures to be performed. The effective amount will be determined on an individual basis and will be based, at least in part, on consideration of the individual's size, the specific tumor, the severity of symptoms to be treated, the result sought, the specific transport agent, the variation of individuals' affinity binding of a given transport agent for its complementary receptors or recognition molecules, etc. Thus, the effective amount can be determined by one of ordinary skill in the art employing such factors and using no more than routine experimentation.

The increase in the transport of a molecule from the bloodstream to the internal spaces of a solid tumor in response to a transport agent relates not only to the quantity of molecules passing from the blood to the tumor, but also, to the type of molecule. The structure and chemical properties of the molecule will affect its transportability.

A method for preparing bradykinin analogs is Merrifield's procedure of solid-phase peptide synthesis (Merrifield, R. B., *J Am. Chem. Soc.*, 86:304 (1964); Draprau, G. and Regoli, D., *Methods in Enzymology*, 163:263–272 (1988)). The first step in a solid-phase synthesis of bradykinin analogs is the formation of a covalent bond between the C-terminal protected amino acid of the chosen peptide sequences and the solid support or resin. The peptide chain is built up residue by residue by repetitive cycles of deprotection, during which the N-terminal Boc-protecting (N-tert-butoxycarbonyl) group is removed by trifluoroacetic acid (TFA). This is followed by neutralization with diisopropylethylamine (DEA) of the amino group left as a salt and coupling of the next amino acid in the sequence. The cycle is repeated until the sequence is completed. After its complete assembly, the peptide is cleaved from the resin and purified.

The chemical synthesis of Cereport™ is shown in U.S. Pat. No. 5,268,164, whose relevant teachings are incorporated herein by reference.

The invention is further illustrated by the following specific examples.

EXEMPLIFICATION

I. Uptake of $^{14}$C-Carboplatin into Solid Tumors

A series of studies were carried out on rat hosts in which suspended tumor cells had been subcutaneously implanted in the flank of the animal to create a solid tumor in situ. The effects of the administration of Cereport™ on the incorporation of $^{14}$C-carboplatin into the tumor were evaluated.

Subjects and Housing Conditions

Male Fischer rats (170–220 g; Taconic Farms, Germantown, N.Y.) were used in these studies. Animals were housed in pairs in polypropylene cages with free access to food and water. The vivarium was maintained on a 12 h light: 12 h dark cycle with a room temperature of 22±1° C. and relative humidity level of 50±5%.

Tumor Cell Maintenance and Implaritation

The MAT B (III) cell line (ATCC CRL-1666), a rat ascites mammary adenocarcinoma, was used to produce peripheral tumors upon implantation in rats. Cells were grown and maintained at 37° C. in a 95% air/5% $CO_2$ humidified atmosphere using McCoy's medium 5A (GIBCO) supplemented with 20 mM HEPES, 1/2X Antibody-Antimycotic, and 10% heat-inactivated Fetal Bovine Serum.

Immediately prior to implantation, MAT B-III cells were suspended in 1.2% methyl cellulose at a density of $5 \times 10^6$/ml. 200 µl of this suspension ($1 \times 10^6$ cells) was injected subcutaneously into the flank of each animal using a 22G needle.

Blood Vessel Cannulation

One week after tumor implantation, and under urethane anesthesia (1.8 g/kg; i.p.), cannulae (PE50, Clay Adams, Bectin Dickinson, Sparks, Md.) were placed in the jugular vein for drug administration and both femoral arteries for the measurement of physiological parameters.

Drug Administration and Physiological Monitoring

Cereport™ (RMP-7, Alkermes, Inc., Cambridge, Mass.) and $^{14}$C-carboplatin or -dextran (SA=144 µCi/mg and 1.08 µCi/mg respectively) were dissolved in sterile 0.9% saline and infused intravenously using a syringe pump at a rate of 0.05 ml/min over the entire administration period. Using the human clinical protocol as a basis, $^{14}$C-carboplatin or dextran (100 µCi/kg) was infused for 15 minutes followed immediately by a 10 minute infusion of Cereport™. Throughout the experiment, body temperature was maintained normothermic (37.0±1.0° C.) and arterial blood gases, pH, and blood pressure were monitored. Animals with physiological values outside the normal ranges were not used.

Tumor Dissection

At the end of the drug administration protocol, rats were sacrificed and the peripheral tumor was rapidly removed. A 1–2 mm thick slice was cut from the center of tumor. The slice was then divided into two equal parts comprising the center of the dissected piece (inner tumor) and the outside edge (outer tumor). Each tumor sample was weighed and placed into a scintillation vial and the amount of radioactivity (nCi/g) was computed for each region using scintillation counts as a measure of the radioactivity.

FIG. 1 shows the uptake of carboplatin (MW 371) into the inner tumor and outer tumor when a bolus of carboplatin was administered two minutes into a ten minute infusion of Cereport™.

For both tumor portions, carboplatin is significantly taken up when Cereport™ is administered. This result is apparent for the three Cereport™ infusion amounts and is in contrast to the uptake result when no Cereport™ is infused.

FIG. 2 shows the uptake of carboplatin into the inner tumor and outer tumor when a bolus of carboplatin is administered two minutes into a five minute infusion of Cereport™.

For both tumor portions, carboplatin is significantly taken up when Cereport™ is administered at 0.75 µg/kg, 1.0 µg/kg, 1.75 µg/kg and 2.5 µg/kg. By contrast, with Cereport™ administration at 0.5 µg/kg and 5.0 µg/kg for five minutes, carboplatin is not significantly taken up, particularly when compared to the result when no Cereport™ is infused. The results depicted in FIG. 2 can be compared to those in FIG. 1 by noting the Cereport™ infusion time.

Figure 3:
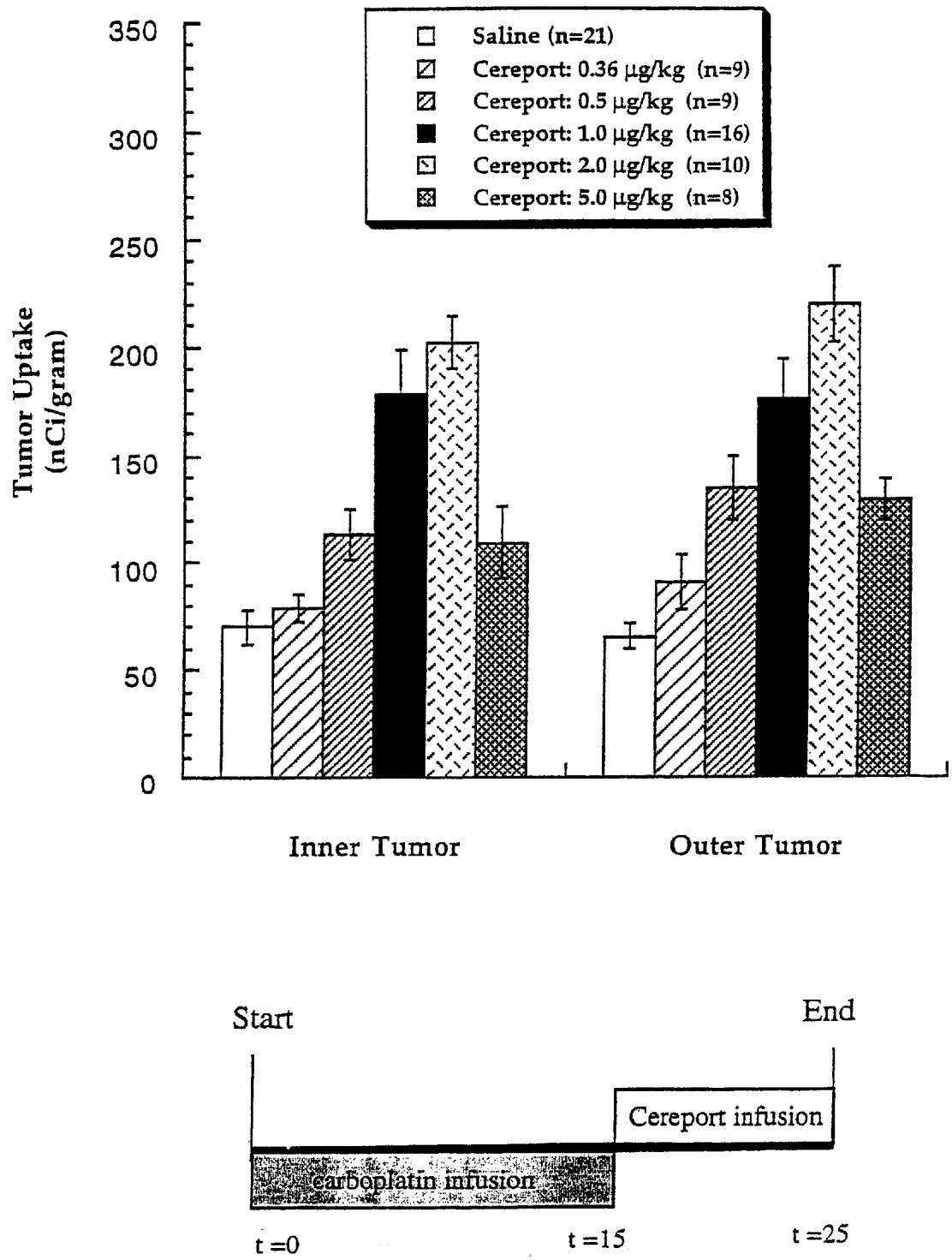
FIG. 3 is another diagrammatic representation of the amount of carboplatin uptake into the inner and outer portions of an implanted tumor for various amounts of administered Cereport™. The sequential time course of carboplatin administration and Cereport™ infusion is also diagrammatically represented.

FIG. 3 shows the uptake of carboplatin into the inner tumor and outer tumor when carboplatin is infused for 15 minutes prior to the administration of Cereport™.

For both tumor portions, carboplatin is significantly taken up when Cereport™ is administered at all doses with the possible exception of 0.36 µg/kg. This result is in contrast to the result when no Cereport™ is infused.

II. Uptake of $^{14}$C-Dextran into Solid Tumors

FIG. 4 shows the uptake of dextran (MW 70 kDa) into inner tumor and outer tumor when dextran is infused for 15 minutes prior to the administration of Cereport™.

For both tumor portions, dextran is significantly taken up when Cereport™ is administered. This result is apparent for the three Cereport™ infusion amounts and is in contrast to the uptake result when no Cereport™ is infused.

III. Uptake of $^{14}$C-Carboplatin in Solid Tumors Located at Different Body Sites MAT B-III cells ($1\times10^6$) were implanted in two anatomically distinct sites in female Fischer rats. The tumor cells were implanted into either the subcutaneous space of the rear flank or orthotopically into mammary fat pads. Seven days later, the animals received a 15 minute i.v. infusion of $^{14}$C-Carboplatin (100 µCi/kg) followed immediately by a 10 minute infusion of either saline or Cereport™ at 1.0 µg/kg. Following the saline or Cereport™ infusion, the tumor was rapidly removed and dissected into inner and outer regions. The amount of radioactivity of each tumor region was determined by scintillation counts.

Figure 5:
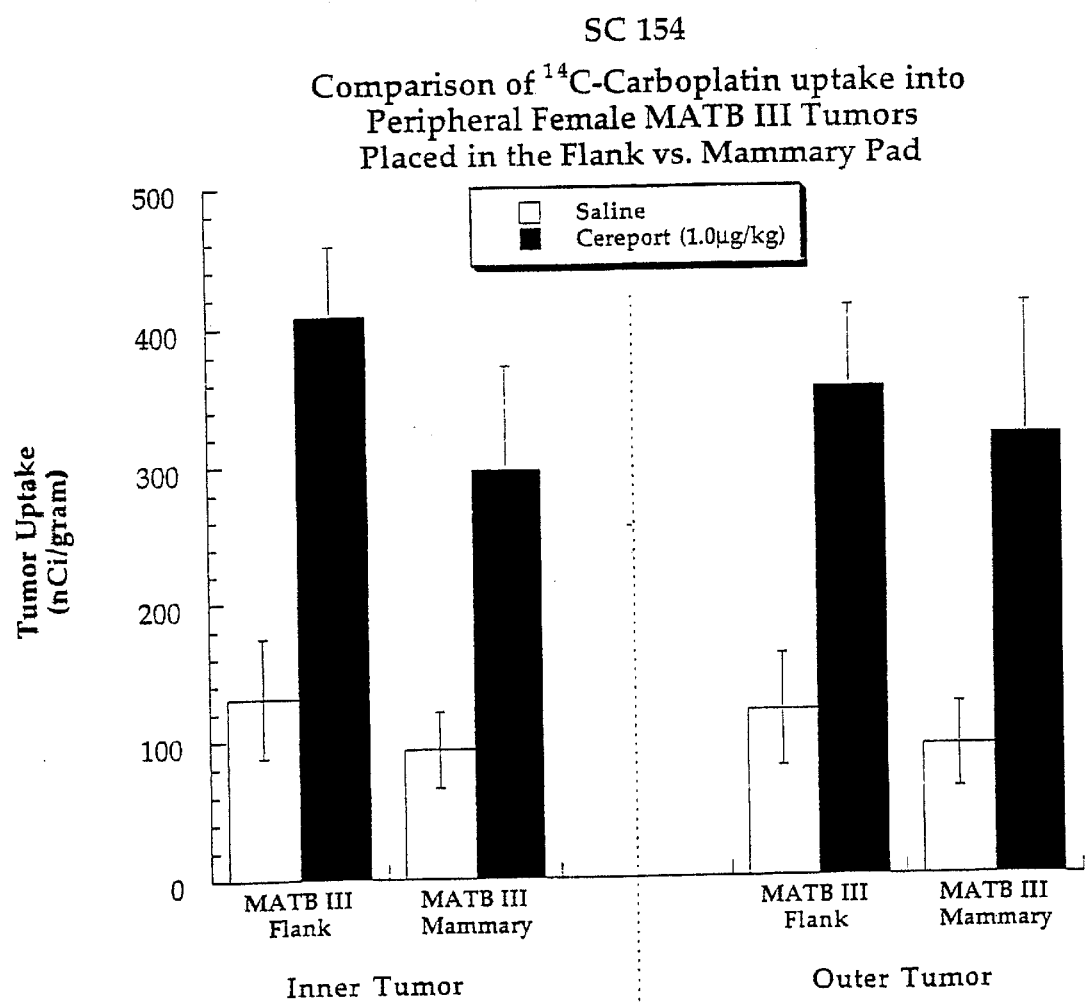
FIG. 5 is a diagrammatic representation of the amount of carboplatin uptake into the inner and outer portions of an implanted tumor when Cereport™ is administered. The tumor was implanted in the flank or in a mammary pad of the host animal.

FIG. 5 shows the uptake of carboplatin into the implanted tumor that is located either in the flank or in the mammary pad. Carboplatin is significantly taken up by the tumor that is located at either site when Cereport™ is infused. These results demonstrate that the anatomic location of the solid tumor does not alter the effect of Cereport™ in increasing the uptake of carboplatin into the tumor.

IV. Uptake of $^{14}$C-Carboplatin in Solid Tumors that Reside Within the Liver MAT B-III cells ($1\times10^6$) were implanted directly into the liver of male Fischer rats using a 25G needle and 1 ml tuberculin syringe. Fourteen days later, the animals received a 15 minute i.v. infusion of $^{14}$C-carboplatin (100 µCi/kg) followed immediately by a 10 minute infusion of either saline or Cereport™ at 1.0 µg/kg. Following the saline or Cereport™ infusion, the liver was rapidly removed. The tumor was dissected free of the surrounding liver tissue and divided into inner and outer regions. A 1 mm strip of liver that immediately surrounded the tumor (inner ring) and the adjacent 1 mm strip of liver (outer ring) were also removed and assayed. In addition, an equivalent strip of liver from the untreated lobe, was removed and assayed. This liver strip served as a control.

Figure 6:
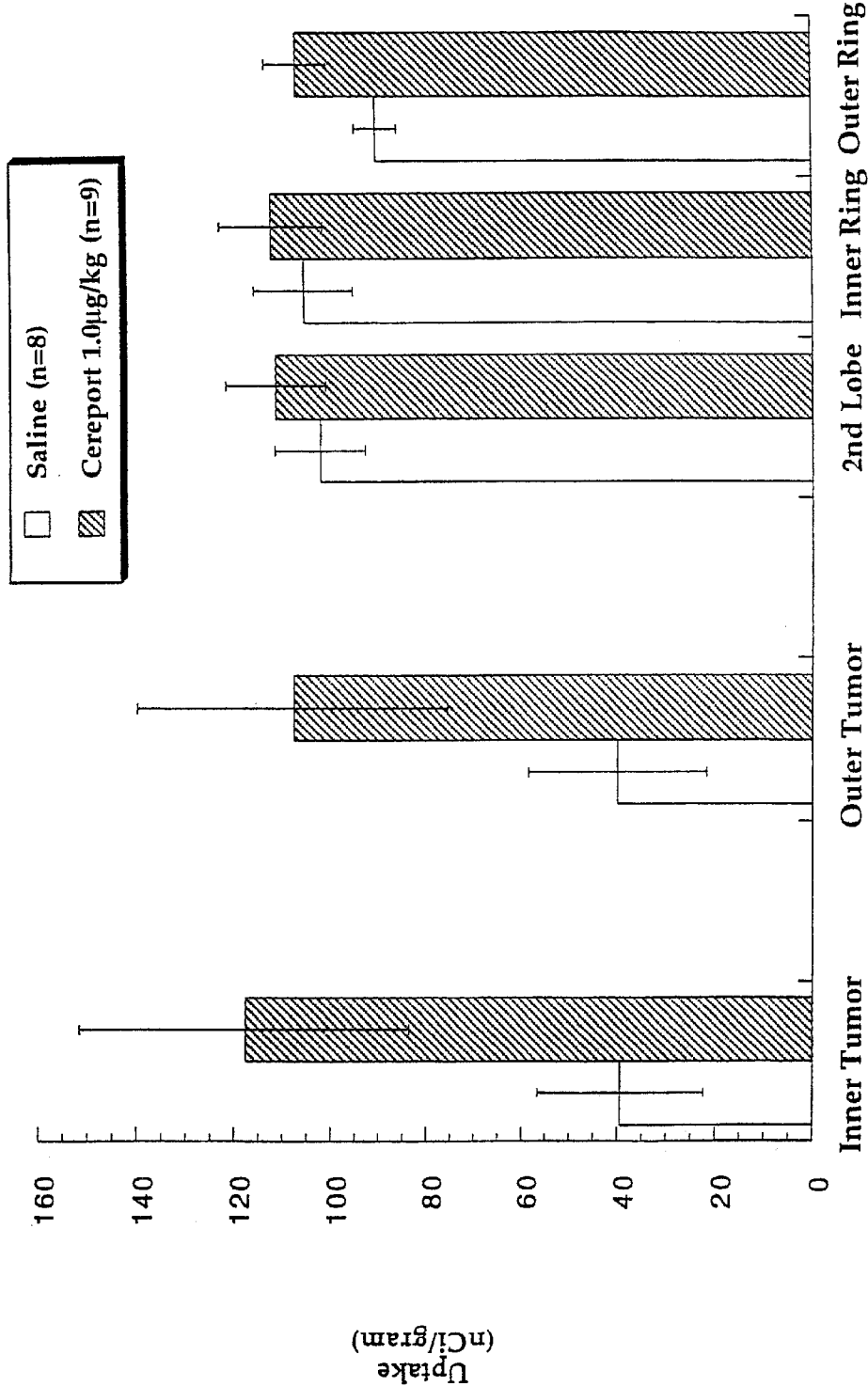
FIG. 6 is a diagrammatic representation of the amount of carboplatin uptake into the inner and outer portions of a tumor that had been implanted in the liver of a host animal. This Figure diagrammatically represents carboplatin uptake into these tumor regions as well as into surrounding portions of the liver when Cereport™ is administered.

FIG. 6 shows the uptake of carboplatin into the implanted tumor and into the adjacent liver strips a well as the control liver strip. Carboplatin is significantly taken up by the tumor when Cereport™ is infused. In contrast, Cereport™ does not have a significant effect on the uptake of carboplatin into the liver tissue that is adjacent to the tumor nor into a control strip of liver. The results indicate that Cereport™ primarily causes carboplatin uptake into tumor tissue, particularly in comparison to the uptake in adjacent non-tumor tissue.

V. Uptake of $^{14}$C-Carboplatin in Solid Tumor and Various Organs

Figure 7:
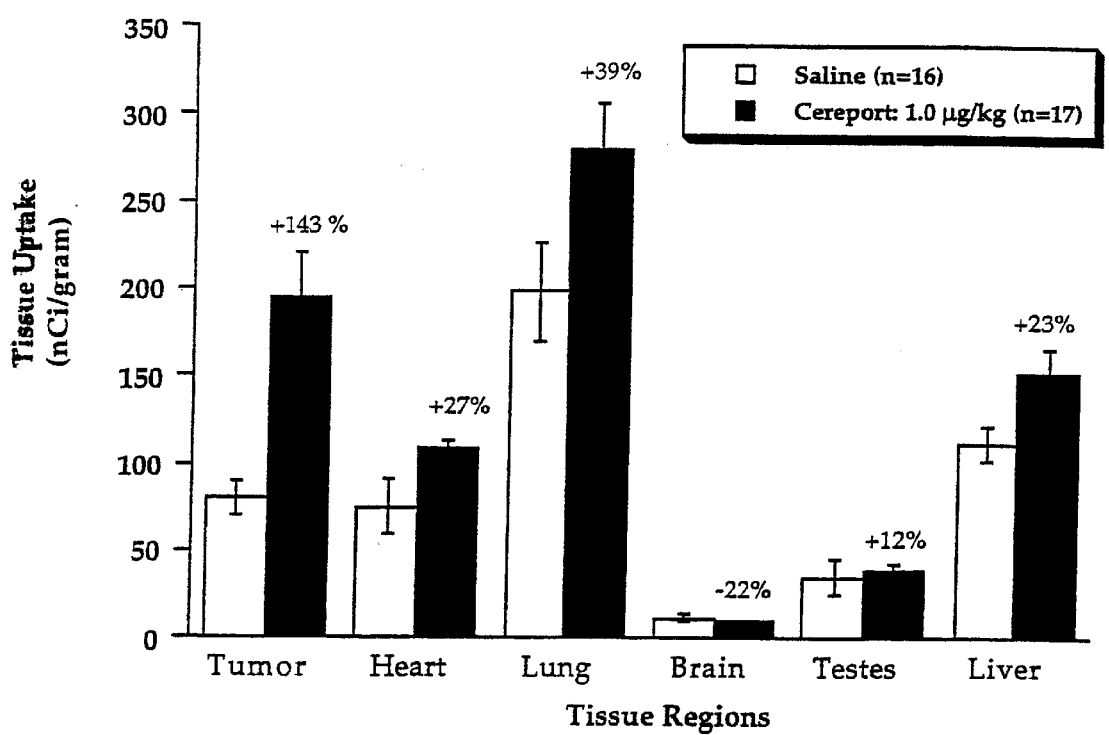
FIG. 7 is a diagrammatic representation of the amount of carboplatin uptake into implanted tumor and various organs when Cereport™ is administered. This uptake is diagrammatically compared to carboplatin uptaken when saline, rather than Cereport™, is administered.

FIG. 7 shows the uptake of carboplatin into the implanted tumor and into various organs when Cereport™, at 1 µg/kg, is administered to the animals. The carboplatin was administered as a bolus two minutes into a five minute Cereport™ infusion.

Although heart, lung and liver show some uptake of carboplatin when Cereport™ is administered, the uptake in tumor tissue far surpasses the uptake into these other noted tissues. It can be concluded that Cereport™ preferentially causes uptake of carboplatin into tumor tissue.

VI. Retention of $^{14}$C-Carboplatin in Solid Tumors and in Lung

Figure 8:
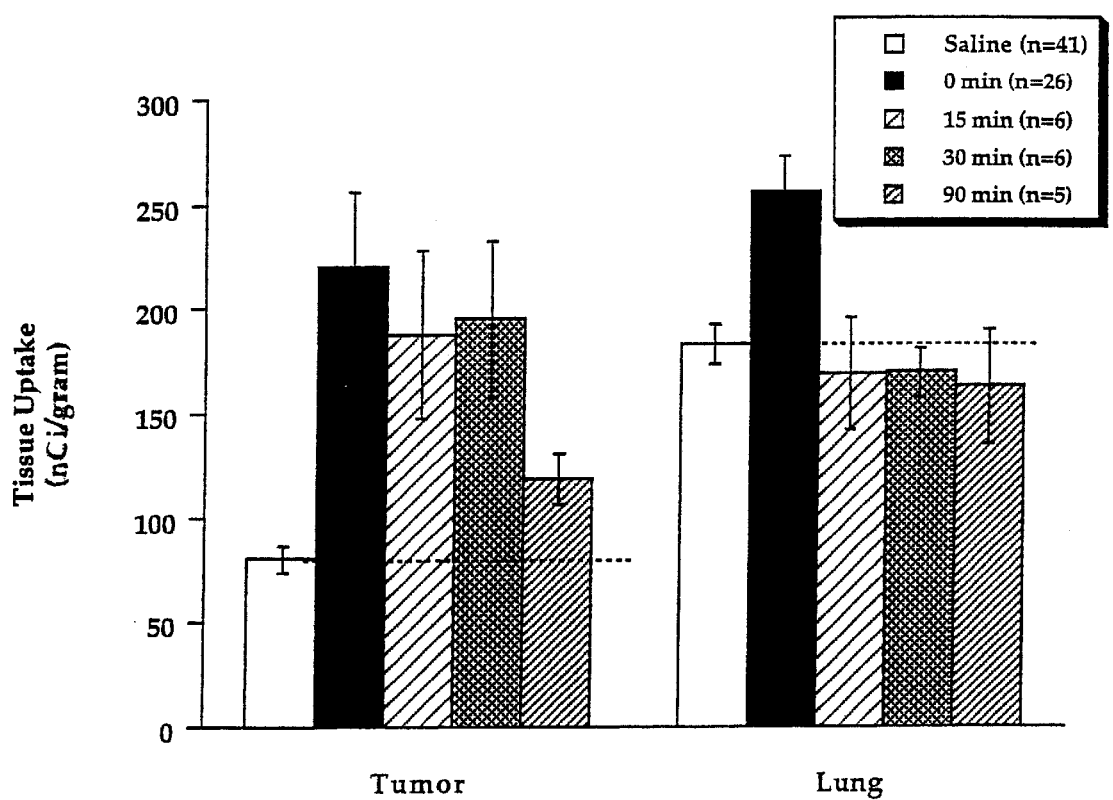
FIG. 8 is a diagrammatic representation of the amount of carboplatin retained in tumor and in non-tumor lung tissue for various times after Cereport™ administration.

FIG. 8 shows the retention of carboplatin in the implanted tumor and in lung following its uptake after Cereport™ administration. The carboplatin was administered two minutes into a five minute Cereport™ infusion.

Carboplatin is retained in tumor tissue for at least 90 minutes. In contrast, carboplatin is not retained by lung after the initial uptake. It should be noted that the carboplatin uptake in lung was one of the few instances where Cereport™ caused carboplatin uptake other than into tumor tissue. These results show that such uptake is transitory except for uptake into tumor tissue.

VII. Uptake of $^{14}$C-Carboplatin in Walker 256 Tumors

Walker 256 cells (ATCC CCL-38) ($1\times10^7$) were implanted into the subcutaneous space of the rear flank of male Wistar rats to create a solid tumor in situ in the same manner as previously described for the MAT B-III cells. Eight days later, the animals received a 15 minute i.v. infusion of $^{14}$C-carboplatin (100 µCi/kg) followed immediately by a 10 minute infusion of either saline or Cereport™ at 1.0 µg/kg. Following the saline or Cereport™ infusion, the tumor was rapidly removed and dissected into inner and outer regions. The amount of radioactivity of each tumor region was determined by scintillation counts.

Figure 9:
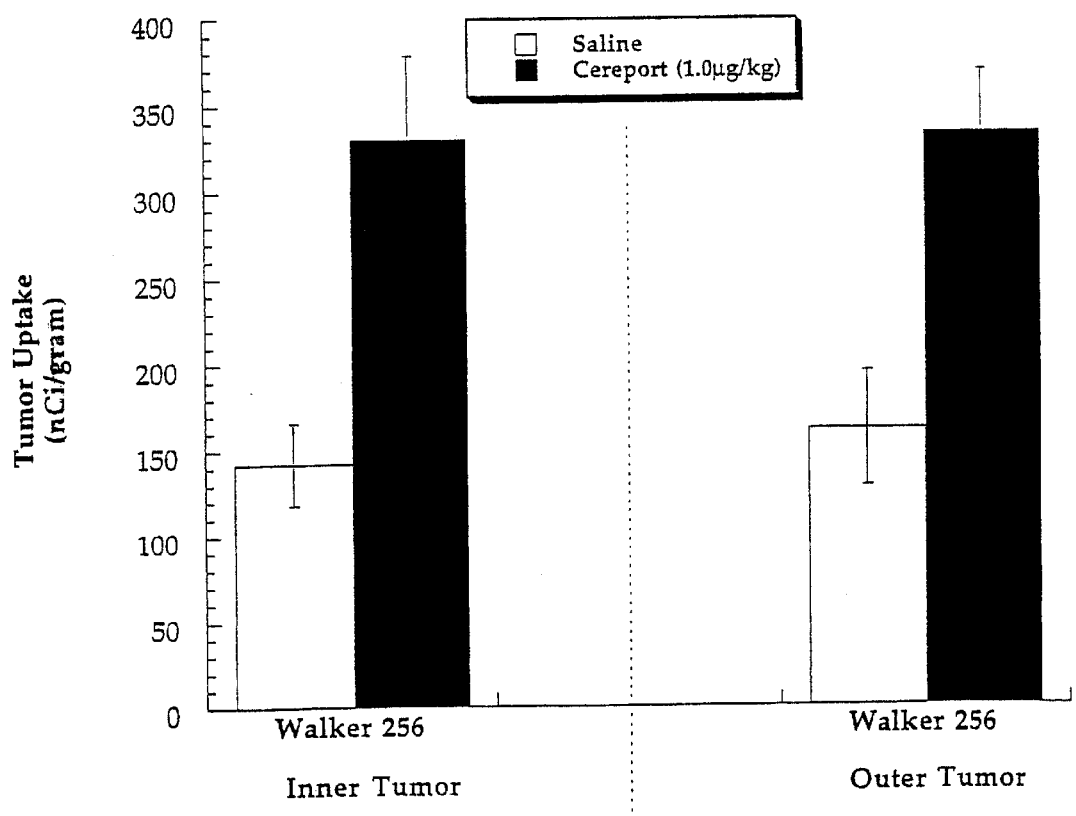
FIG. 9 is a diagrammatic representation of the amount of carboplatin uptake into the inner and outer portions of an implanted Walker 256 tumor when Cereport™ is administered.

FIG. 9 shows the uptake of carboplatin into the inner region and outer region of the implanted tumor. Carboplatin is significantly taken up when Cereport™ is administered. These results show that the increased uptake of carboplatin due to Cereport™ administration is not tumor type specific. Different peripheral solid tumors take up carboplatin when Cereport™ is administered.

Figure 10:
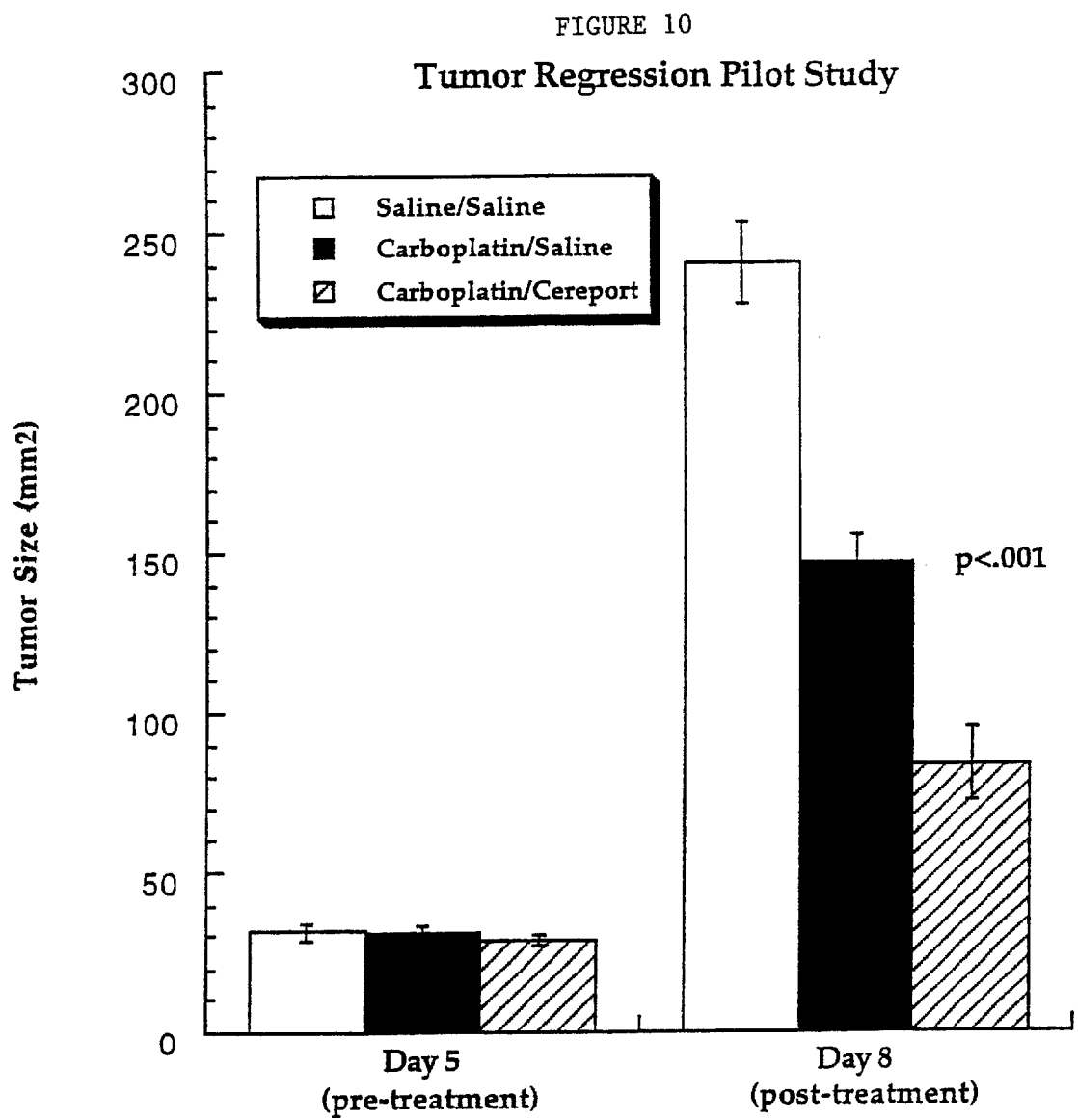
FIG. 10 is a diagrammatic representation of the size of an implanted tumor before and after administration of carboplatin with and without Cereport™. This Figure diagrammatically represents saline control values, carboplatin plus saline, and carboplatin plus Cereport™.

VIII. Tumor Regression After $^{14}$C-Carboplatin and Cereport™ Administration FIG. 10 shows the regression of tumor size when carboplatin is administered to the animal. In some instances, Cereport™ is administered in addition to carboplatin. The carboplatin was infused for 15-minutes followed immediately by a 10 minute infusion of Cereport™ at 1.5 µg/kg.

The administration of Cereport™ and carboplatin markedly cause regression of the implanted tumor in comparison to the administration of carboplatin alone. By the eighth day (when carboplatin and Cereport™ were administered), the tumor had shrunk to approximately one third of the size it would have had if no carboplatin had been administered, and to approximately one half the size it would have had if Cereport™ had not been administered with the carboplatin. These results demonstrate that Cereport™ markedly affects the efficacy of carboplatin on tumor regression, apparently by causing increased uptake of carboplatin by the tumor.

IX. Metastatic Lung Tumor Implantation and Prolonged Animal Survival Following Carboplatin and Cereport™ Administration MAT B-III cells were introduced into the lungs of 12 female F-344 Fisher rats by intrajugular injections of either $1\times10^5$ or $1\times10^6$ cells in 200 µl suspensions. The cells and animals were maintained and handled as described in Example 1. At various times following the injections, the number of surface tumor colonies on the lungs was assessed. Tumors were visually counted by injecting India ink into the trachea of the animals. The lung tissue was blackened by the ink thereby revealing the tumors which remain white because they do not absorb the ink.

Figure 11:
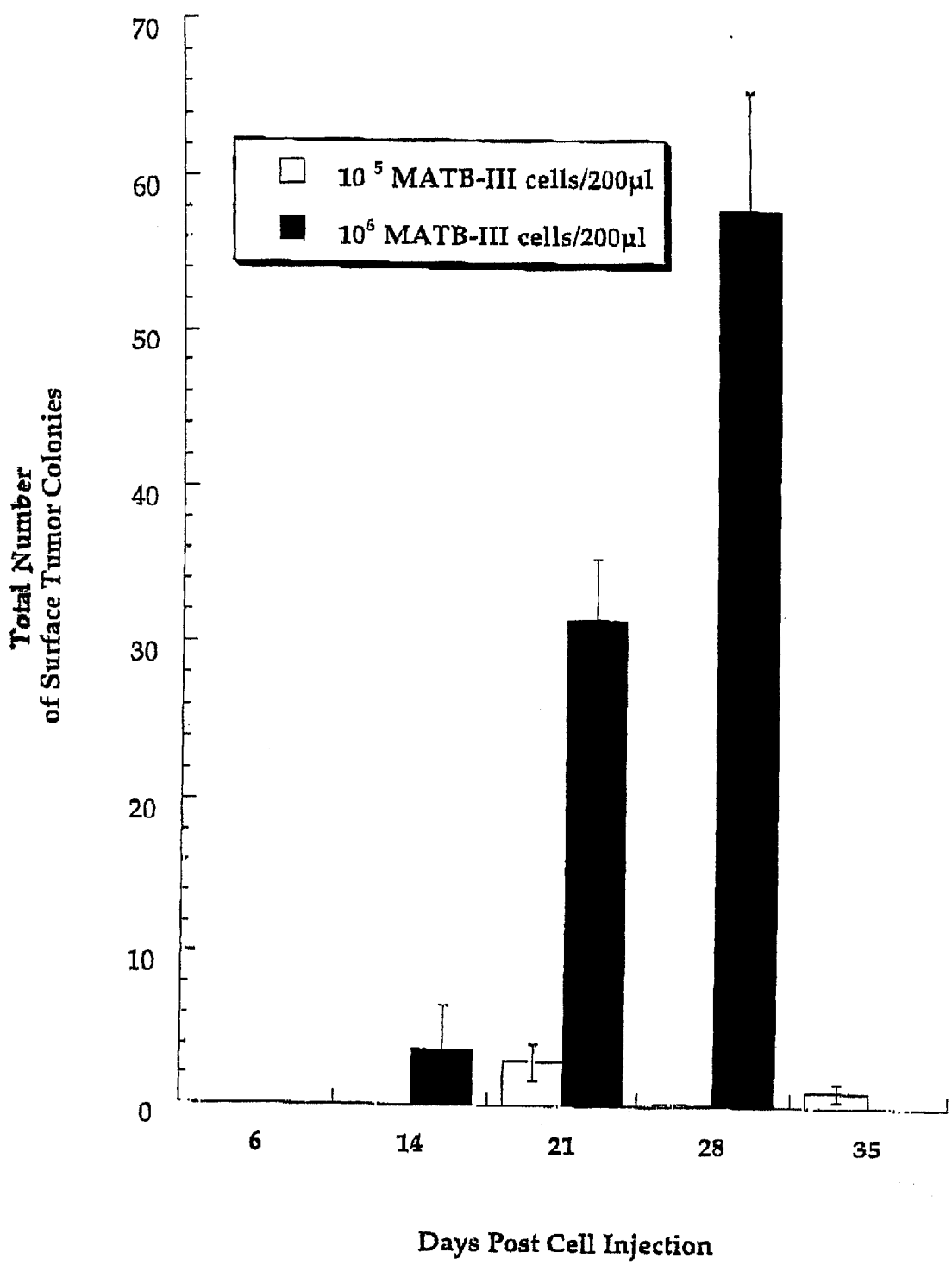
FIG. 11 is a diagrammatic representation of the numbers of metastatic lung tumors that are present at various times after the injection of either $1 \times 10^5$ or $1 \times 10^6$ MAT B-III cells.

The results of these lung tumor colony assessments are shown in FIG. 11. These results show that the injection of $1\times10^6$ MAT B-III cells is followed by an increase of the number of metastatic lung tumors in these animals as time progresses following the initial cell injection. In contrast, the number of metastatic lung tumors in these animals diminishes with time following cell injection when $1\times10^6$ MAT B-III cells are initially injected.

The metastatic lung tumors that form following intrajugular injections of MAT B-III cells have various sizes. The individual sizes of the metastatic lung tumors were visually assessed at various times following the injection of $1\times10^6$ MAT B-III cells. These individual metastatic lung tumor size measurements were placed in the arbitrarily chosen size categories of <1 mm, 1–3 mm, and >3 mm.

Figure 12:
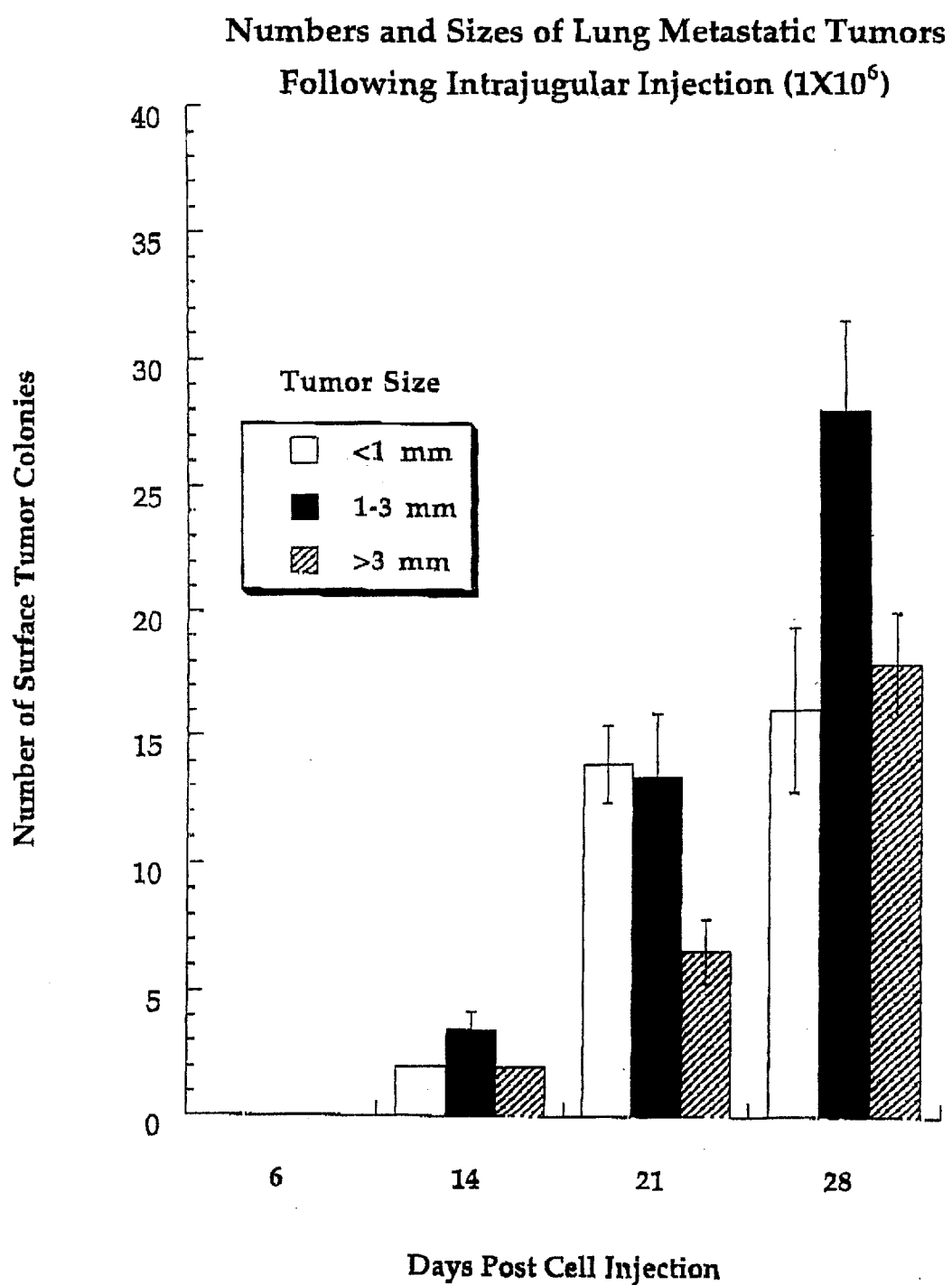
FIG. 12 is a diagrammatic representation of numbers and sizes of metastatic lung tumors that are present at various times after the injection of $1 \times 10^6$ MAT B-III cells.

The results of these size measurement assessments are shown in FIG. 12. It is apparent from these results that the metastatic lung tumor sizes cluster around the 1–3 mm size. This tumor size clustering does not vary significantly as time progresses from the initial MAT B-III cell suspension injection. However, as previously shown, the total number of surface tumor colonies does increase as time progresses from the initial cell injection. Likewise, by necessity, the number of surface tumor colonies in each of the size categories also increases. Thus, it can be concluded that metastasis of the surface lung tumors occurs, but.the size of the surface tumor colonies remains relatively invariant, clustering around 1–3mm, as time progresses following tumor cell injection.

Finally, the effects of the administration of carboplatin and Cereport™ on the survival of animals who had been subjected to the implantation of MAT B-III metastatic lung surface tumors was assessed. In this study, $1\times10^6$ MAT B-III cells as a 200 µl suspension were implanted by intrajugular injection in 54 male Fischer rats. Sixteen days later, indwelling cannulae were inserted in the previously implanted jugular vein. On days 16 and 23, the animals received a continuous infusion of 5 mg/kg of carboplatin over a 15 minute period. Immediately following the 15 minute carboplatin infusion, the animals received a 10 minute continuous infusion of either saline or Cereport (1.5 µg/kg). The survival rates for the animals were then monitored.

Figure 13:
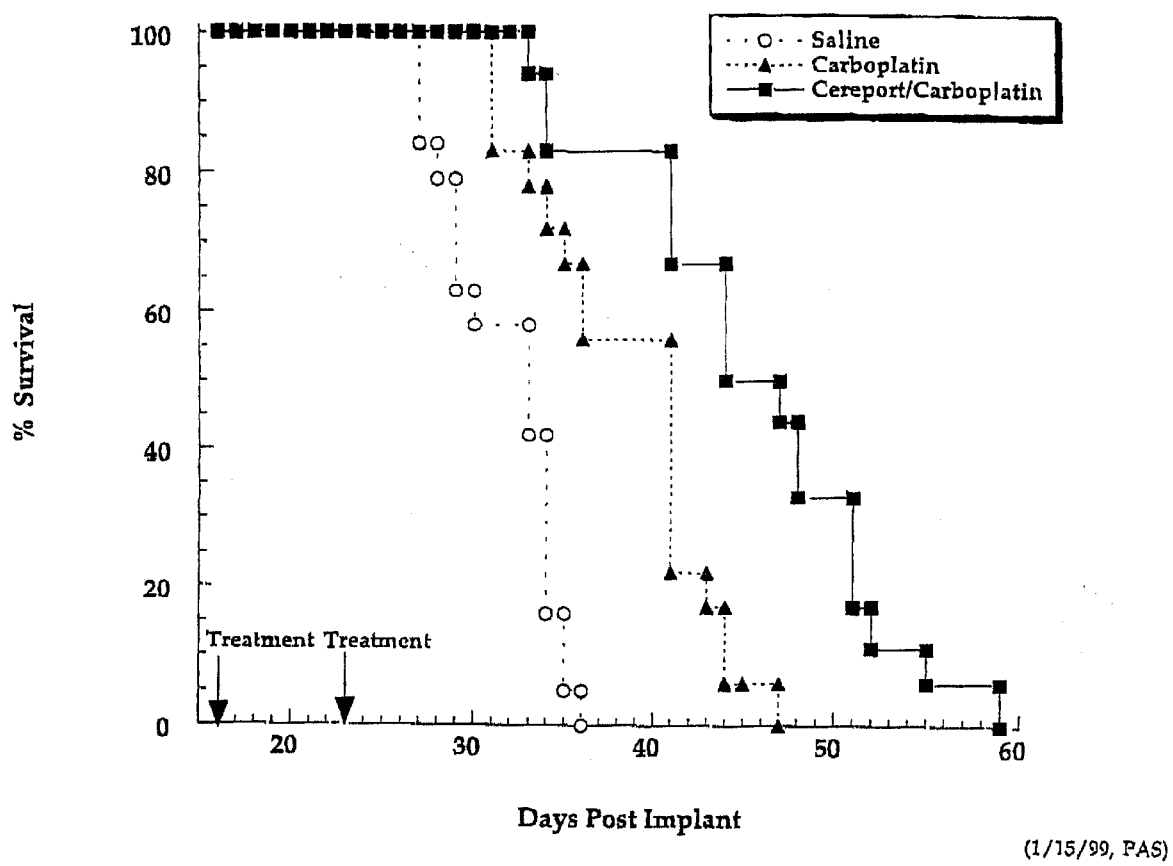
FIG. 13 is a graphical representation of the percent surviving animals following the injection of $1 \times 10^6$ MAT B-III cells when saline, carboplatin, or a specified sequence of carboplatin and Cereport™ is administered at two time points after the tumor cell injection. The percent surviving animals was assessed daily after the tumor cell injection.

The results of this study are displayed in FIG. 13. It is readily apparent that total mortality occurs approximately 35 days after injection of the MAT B-III cells if the antitumor agent, carboplatin, is not administered. The administration of this antitumor agent, by itself, will prolong survival for approximately 10 days. However, when Cereport™ is administered in addition to carboplatin, the survival profile is extended for about an additional 10 days. Thus, it is clear that Cereport™ has a marked therapeutic effect on the survival of animals who have metastatic lung tumors, probably by causing an increased uptake and/or retention of carboplatin into the tumor masses.

X. Interstitial Fluid Pressure When Cereport™ is Infused

Figure 14:
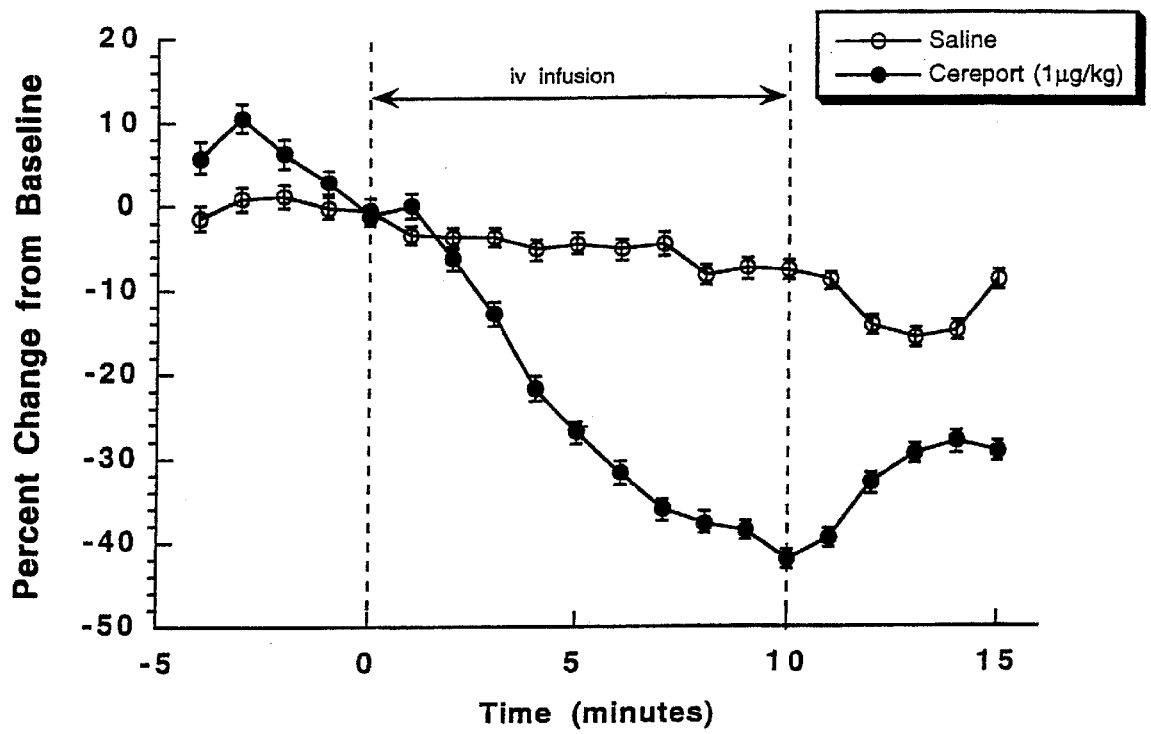
FIG. 14 is a graphical depiction of the percent change from baseline (normal) values at zero time for the interstitial fluid pressure (IFP) in implanted tumors when either saline or Cereport™ is infused.

FIG. 14 shows the effect of Cereport™ on the interstitial fluid pressure (IFP) of the implanted tumor.

Interstitial fluid pressure is a severe impediment for administered substances into tumor interstitial spaces from the bloodstream. Infusion of Cereport™ for 10 minutes at 1 µg/kg causes the interstitial fluid pressure in implanted tumors to decrease by up to 40%. This decrease in interstitial fluid pressure strongly correlates with uptake of substances such as carboplatin or dextran.

XI. Effect of $B_2$ Receptor Blocking on the Uptake of Carboplatin into Tumors

MAT B-III cells ($1\times10^6$) were implanted into the subcutaneous space of the rear flank of male Fisher rats. Seven days later, the animals received a 15 minute i.v. infusion of $^{14}$C-carboplatin (100 µCi/kg) followed immediately by a 10 minute infusion of either saline or Cereport™. Following the saline or Cereport™ infusion, the tumor was rapidly removed and dissected into inner and outer regions. The amount of radioactivity of each tumor region was determined by scintillation counts.

In one set of experiments, the $B_2$ receptor blocking agent D-Arg[Hyp$^3$-Thi$^5$-D-Tic$^7$-Oic$^8$] (HOE-140) (100 µg/kg) was infused for 15 minutes starting 5 minutes prior to the Cereport™ infusion (1.0 1µg/kg) and extending throughout the 10 minute Cereport™ infusion.

Figure 15:
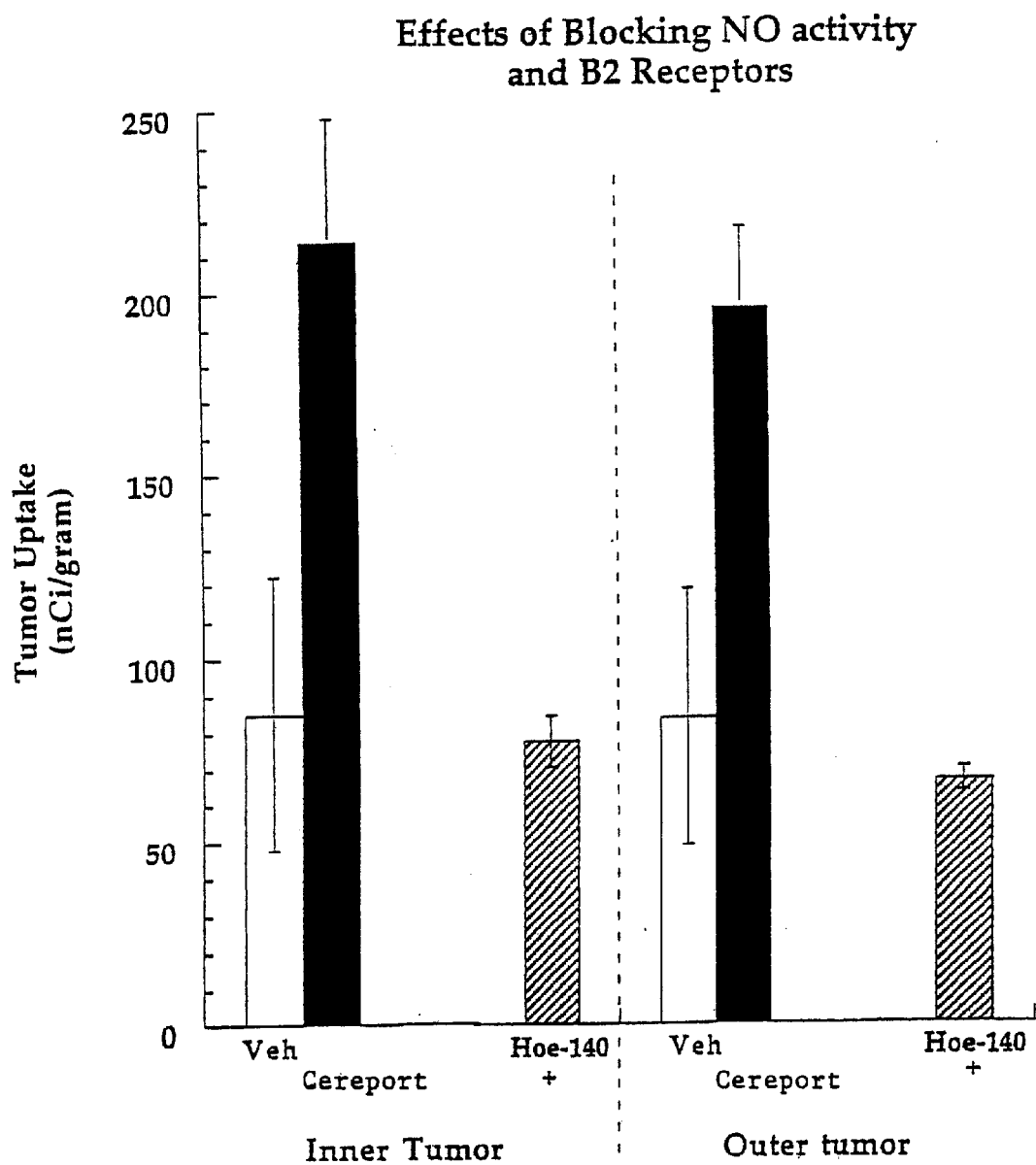
FIG. 15 is a diagrammatic representation of the amount of carboplatin uptake into the inner and outer portions of an implanted tumor when Cereport is administered. This Figure diagrammatically represents the carboplatin uptake into the tumor regions when a $B_2$ receptor antagonist, HOE-140, is present in addition to Cereport™.

FIG. 15 shows the uptake of carboplatin into the inner region and outer region of the implanted tumor when Cereport™ is administered. However, when the $B_2$ blocking agent, HOE-140, is also administered, the carboplatin uptake effects of Cereport™ are nullified. These results indicate that binding of Cereport™ to the $B_2$ receptors is intimately associated with the uptake of carboplatin by tumors that are caused by the presence of Cereport™.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for delivering a pharmaceutical or diagnostic substance to a non-central nervous system solid tumor in a host comprising co-administering intravascularly to said host said substance and an effective amount of a bradykinin agonist, which is a bradykinin agonist, that increases the transport of said substance from the bloodstream of said host to the internal spaces of said non-central nervous system solid tumor.

2. The method of claim 1 wherein the host is a human being.

3. The method of claim 1 wherein said bradykinin analog comprises a peptide with the amino acid sequence of $NH_2$-arginine-proline-hydroxyproline-glycine-thienylalanine-serine-proline-4-Me-tyrosine$\psi(CH_2NH)$arginine-COOH (SEQ ID NO: 1) or a conformational analog thereof.

4. The method of claim 3 wherein said conformational analog is said peptide with at least one of the following modifications:

a) the N-terminal arginine is replaced by an amino acid analog containing a guanidino or guanidino derivative side chain;

b) the second amino acid (proline) is replaced by hydroxyproline, dehydroproline, N-methylalanine or another proline analog;

c) the third amino acid (hydroxyproline) is replaced by proline, dehydroproline, another proline analog, alanine, sarcosine or N-methylalanine;

d) the fifth amino acid (thienylalanine) is replaced by another aromatic amino acid or a hydrophobic aliphatic amino acid;

e) the sixth amino acid (serine) is replaced by glycine, threonine, alanine, allo-threonine, asparagine, glutamine or analogs thereof;

f) the seventh amino acid (proline) is replaced by hydroxyproline, dehydroproline, N-methylalanine or another proline analog;

g) the eighth amino acid (4-Me-tyrosine) is replaced by another O-alkyl tyrosine or a hydrophobic aliphatic amino acid;

h) the C-terminal arginine is replaced by an amino acid analog containing a guanidino or guanidino derivative side chain; and i) the peptidomimetic isosteric bond between the eighth amino acid (4-Me-tyrosine) and the C-terminal arginine ($\psi(CH_2NH)$ is replaced by $\psi(CSNH)$, $\psi(NHCO)$ or $\psi(CH_2S)$.

5. The method of claim 4 wherein said modification is chosen from:

a) β-cycloarginine, homoarginine, γ-hydroxyarginine, canavanine, $N^\omega$-amidinocitrulline, 2-amino-4-guanidinobutanoic acid, a cyanoguanidino derivative of lysine or ornithine, citrulline or homocitrulline for the N-terminal or C-terminal arginine;

b) hydroxyproline or dehydroproline for the second or seventh amino acids (proline);

c) proline or dehydroproline for the third amino acid (hydroxyproline);

d) dehydrophenylalanine, phenylalanine or another aromatic analog, leucine, isoleucine or cyclohexylalanine for the fifth amino acid (thienylalanine);

e) glycine or threonine for the sixth amino acid (serine); and f) O-alkyl tyrosine, leucine, isoleucine or cyclohexylalanine for the eighth amino acid (4-Me-tyrosine).

6. The method of claim 3 wherein all optically active amino acids are of the L-configuration.

7. The method of claim 3 wherein the eighth amino acid is of the D-configuration.

8. The method of claim 3 wherein either acetylating groups, additional amino acids or acetylated additional amino acids are attached through a peptide bond to said N-terminal arginine.

9. The method of claim 1 wherein said pharmaceutical or diagnostic substance is administered intravenously.

10. The method of claim 1 wherein said bradykinin analog is administered intravenously.

11. The method of claim 1 wherein said pharmaceutical or diagnostic substance and said bradykinin analog are co-administered simultaneously to said host.

12. The method of claim 1 wherein said pharmaceutical or diagnostic substance is administered to said host during the time that said bradykinin analog is administered.

13. The method of claim 1 wherein said pharmaceutical or diagnostic substance and said bradykinin analog are co-administered sequentially to said host.

14. The method of claim 13 wherein said pharmaceutical or diagnostic substance is administered to said host prior to the administration of said bradykinin analog.

15. The method of claim 1 wherein said diagnostic substance comprises a diagnostic imaging substance.

16. The method of claim 15 wherein said diagnostic imaging substance is radiolabelled.

17. The method of claim 1 wherein said pharmaceutical substance is a therapeutically active substance.

18. The method of claim 17 wherein said therapeutically active substance is a chemotherapeutic substance.

19. The method of claim 17 wherein said therapeutically active substance is a hydrophilic substance that retards tumor growth.

20. A method for delivering a pharmaceutical or diagnostic substance present in the bloodstream of a host to a non-central nervous system solid tumor in said host comprising administering intravascularly to said host an effective amount of a bradykinin analog, which is a bradykinin agonist, that increases the transport of said substance from the bloodstream of said host to the internal spaces of said non-central nervous system solid tumor under conditions whereby said substance and said bradykinin analog are present simultaneously in the bloodstream of said host.

* * * * *

UNITED STATES PATENT AND TRADEMARK OFFICE
CERTIFICATE OF CORRECTION

PATENT NO.    : 6,630,120 B1
DATED         : October 7, 2003
INVENTOR(S)   : Raymond T. Bartus and Dwine F. Emerich It is certified that error appears in the above-identified patent and that said Letters Patent is hereby corrected as shown below:

<u>Column 15,</u>
Line 44, delete the first word, "agonist", and insert therefor -- analog --.

Signed and Sealed this

Eleventh Day of November, 2003

JAMES E. ROGAN
*Director of the United States Patent and Trademark Office*